(12) United States Patent
Mousa et al.

(10) Patent No.: US 9,950,091 B2
(45) Date of Patent: Apr. 24, 2018

(54) COMPOSITION AND METHOD FOR STOPPING HEMORRHAGE, INFECTION, AND ACCELERATING HEALING IN VARIOUS TYPES OF WOUND OR BURNS

(71) Applicants: Deena S. Mousa, Wynantskill, NY (US); Shaker A. Mousa, Wynantskill, NY (US)

(72) Inventors: Deena S. Mousa, Wynantskill, NY (US); Shaker A. Mousa, Wynantskill, NY (US)

(*) Notice: Subject to any disclaimer, the term of this patent is extended or adjusted under 35 U.S.C. 154(b) by 0 days.

(21) Appl. No.: 15/001,385

(22) Filed: Jan. 20, 2016

(65) Prior Publication Data
US 2016/0206773 A1 Jul. 21, 2016

Related U.S. Application Data

(60) Provisional application No. 62/105,465, filed on Jan. 20, 2015.

(51) Int. Cl.

| | | |
|---|---|---|
| *A61K 31/728* | (2006.01) | |
| *A61K 31/734* | (2006.01) | |
| *A61L 15/44* | (2006.01) | |
| *A61K 38/48* | (2006.01) | |
| *A61K 31/195* | (2006.01) | |
| *A61K 31/137* | (2006.01) | |
| *A61K 33/14* | (2006.01) | |
| *A61L 26/00* | (2006.01) | |
| *A61L 15/58* | (2006.01) | |
| *A61L 24/00* | (2006.01) | |
| *A61L 24/10* | (2006.01) | |

(52) U.S. Cl.
CPC ............ *A61L 15/44* (2013.01); *A61K 31/137* (2013.01); *A61K 31/195* (2013.01); *A61K 33/14* (2013.01); *A61K 38/4833* (2013.01); *A61L 15/58* (2013.01); *A61L 24/0015* (2013.01); *A61L 24/0094* (2013.01); *A61L 24/106* (2013.01); *A61L 26/008* (2013.01); *A61L 26/0066* (2013.01); *A61L 26/0076* (2013.01); *A61L 26/0095* (2013.01); *A61L 2300/402* (2013.01); *A61L 2300/406* (2013.01); *A61L 2300/412* (2013.01); *A61L 2300/418* (2013.01); *A61L 2400/04* (2013.01); *A61L 2400/12* (2013.01); *A61L 2430/34* (2013.01); *C12Y 304/21005* (2013.01)

(58) Field of Classification Search
None
See application file for complete search history.

(56) References Cited

U.S. PATENT DOCUMENTS

| | | | |
|---|---|---|---|
| 2006/0216266 A1* | 9/2006 | Liu | A61L 24/06 424/78.27 |
| 2010/0254900 A1* | 10/2010 | Campbell | A61L 27/18 424/1.65 |
| 2012/0148522 A1* | 6/2012 | Schlenoff | A61L 15/42 424/78.35 |

FOREIGN PATENT DOCUMENTS

| | | | |
|---|---|---|---|
| CN | 102600019 A * | 7/2012 | |
| WO | WO 2013048787 A1 * | 4/2013 | A61L 15/44 |

OTHER PUBLICATIONS

English translation of CN102600019A retrieved from Espacenet on Apr. 10, 2017.*
Marisch, E.; Travan, A.; Feresini, M.; Lapasin, R.; Paoletti, S.; Donati, I. Polysaccharide-based polyanion-polycation-polyanion-ternary systems in the concentrated regime and hydrogel form. Macromol. Chem. Phys. 2013, 214, 1309-1320.*
"Blood thinners: Warfarin, heparin, Novel Oral Anticoagulant Drugs (NOAC)", retrieved on Jan. 17, 2018 from the Internet: <URL: https://www.webmd.boots.com/heart-disease/guide/warfarin-heparin-blood-thinners >, 2 pages.

* cited by examiner

*Primary Examiner* — Jessica Worsham
(74) *Attorney, Agent, or Firm* — Schmeiser, Olsen & Watts

(57) ABSTRACT

A composition and a method of applying the composition to a site on or within a body of a mammal. The composition includes a hydrogel matrix that includes at least one polymer cross linked, via ionic or covalent bonding, with both hyaluronic acid and alginic acid. The at least one polymer is chitosan, poly L-Lysine, or a combination thereof.

21 Claims, 15 Drawing Sheets

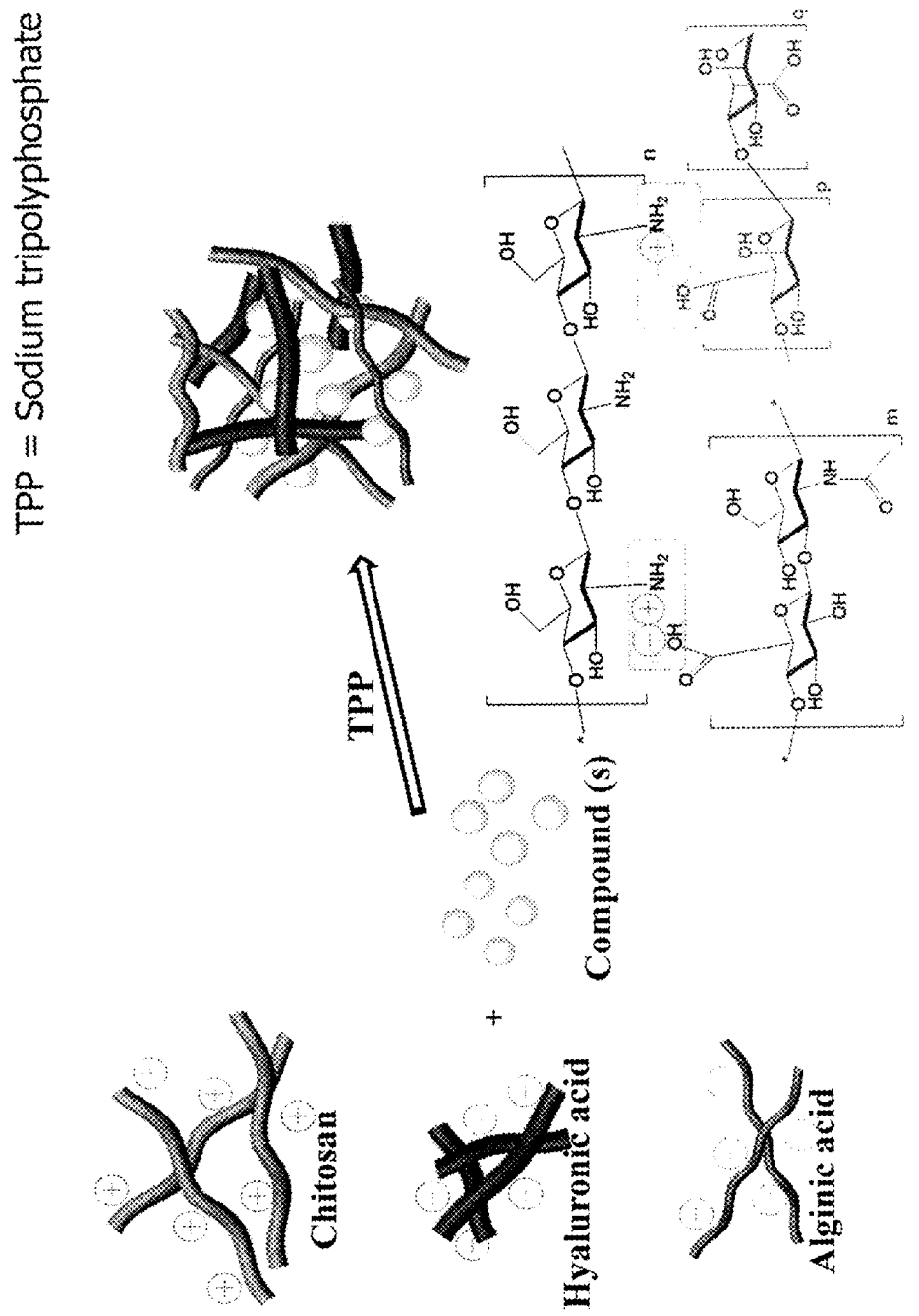
Figure 1A (Ionic Bonding)

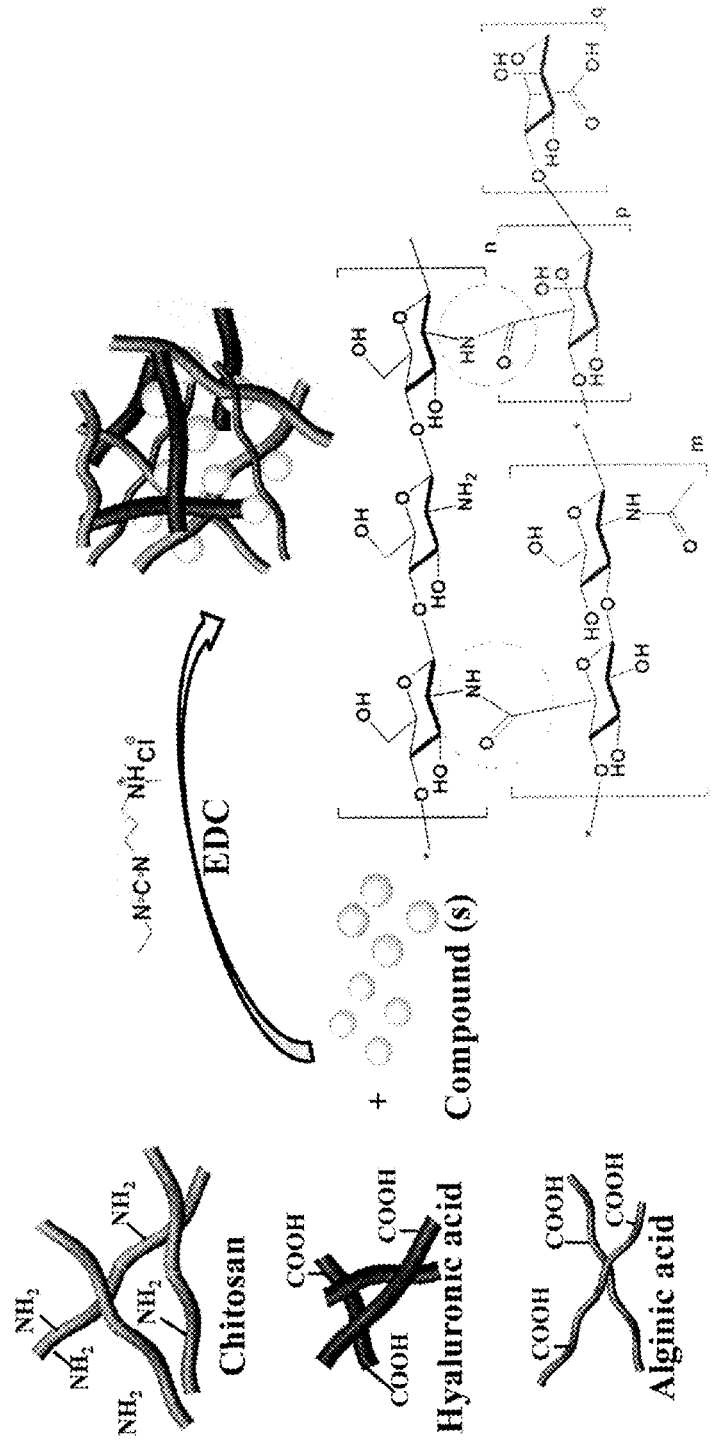
Figure 1B (Covalent Bonding)

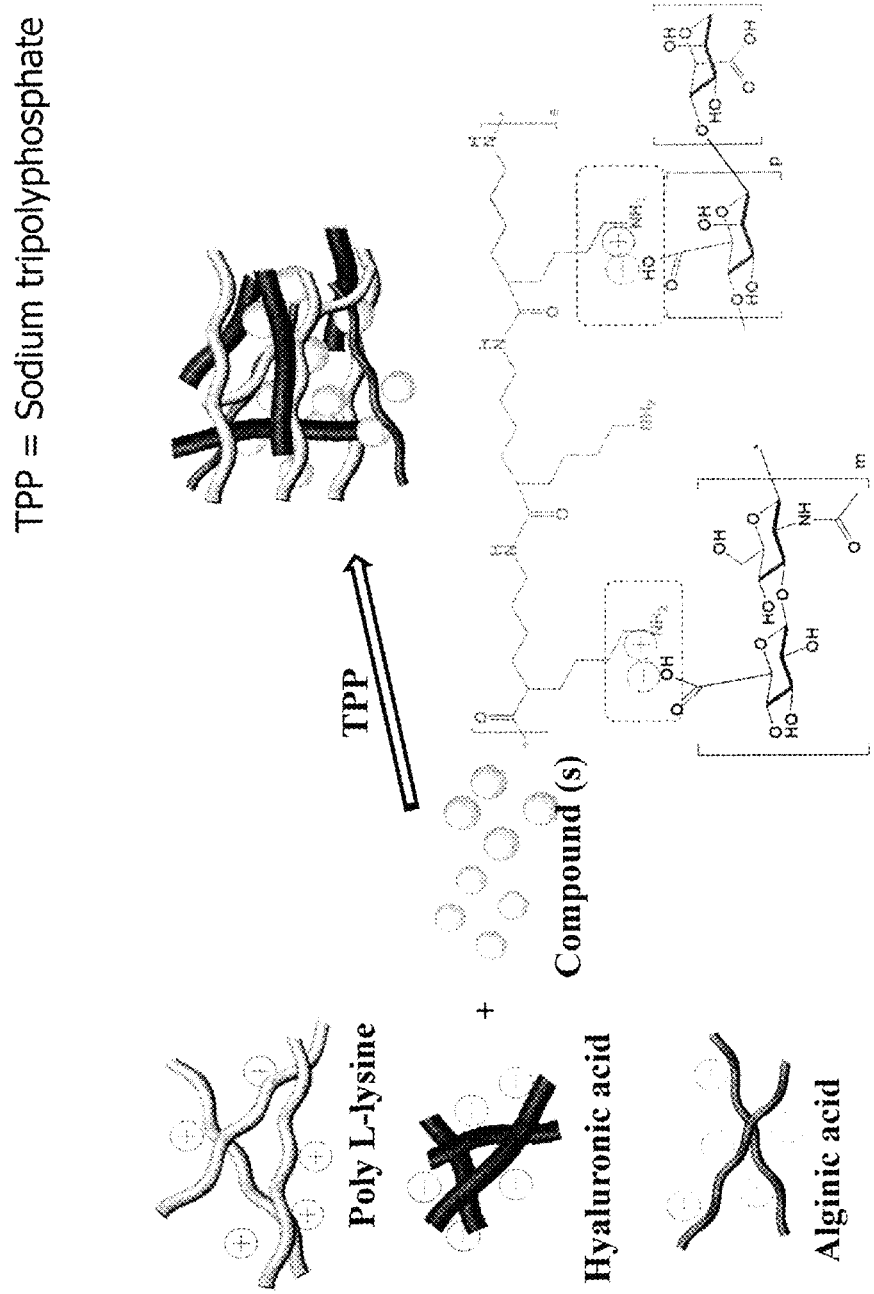
Figure 2A (Ionic Bonding)

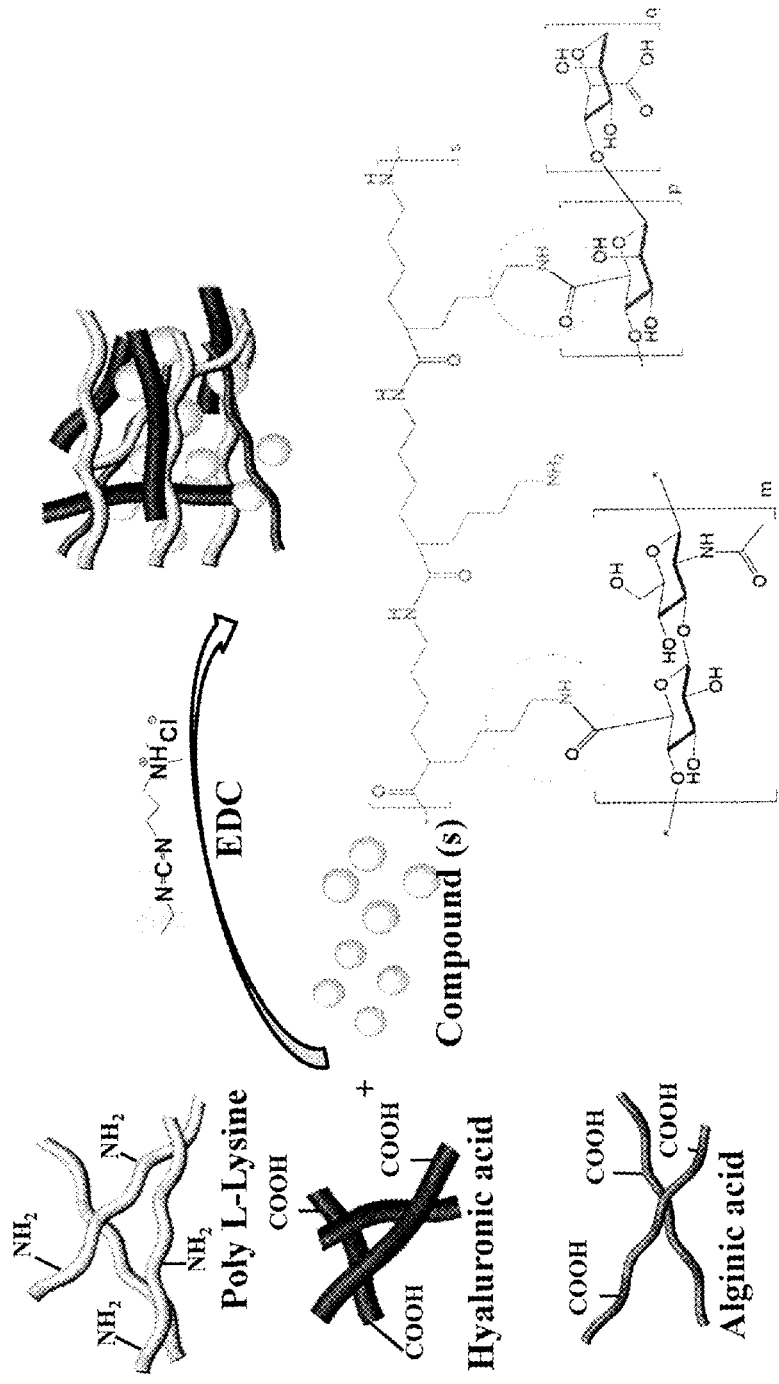
Figure 2B (Covalent Bonding)

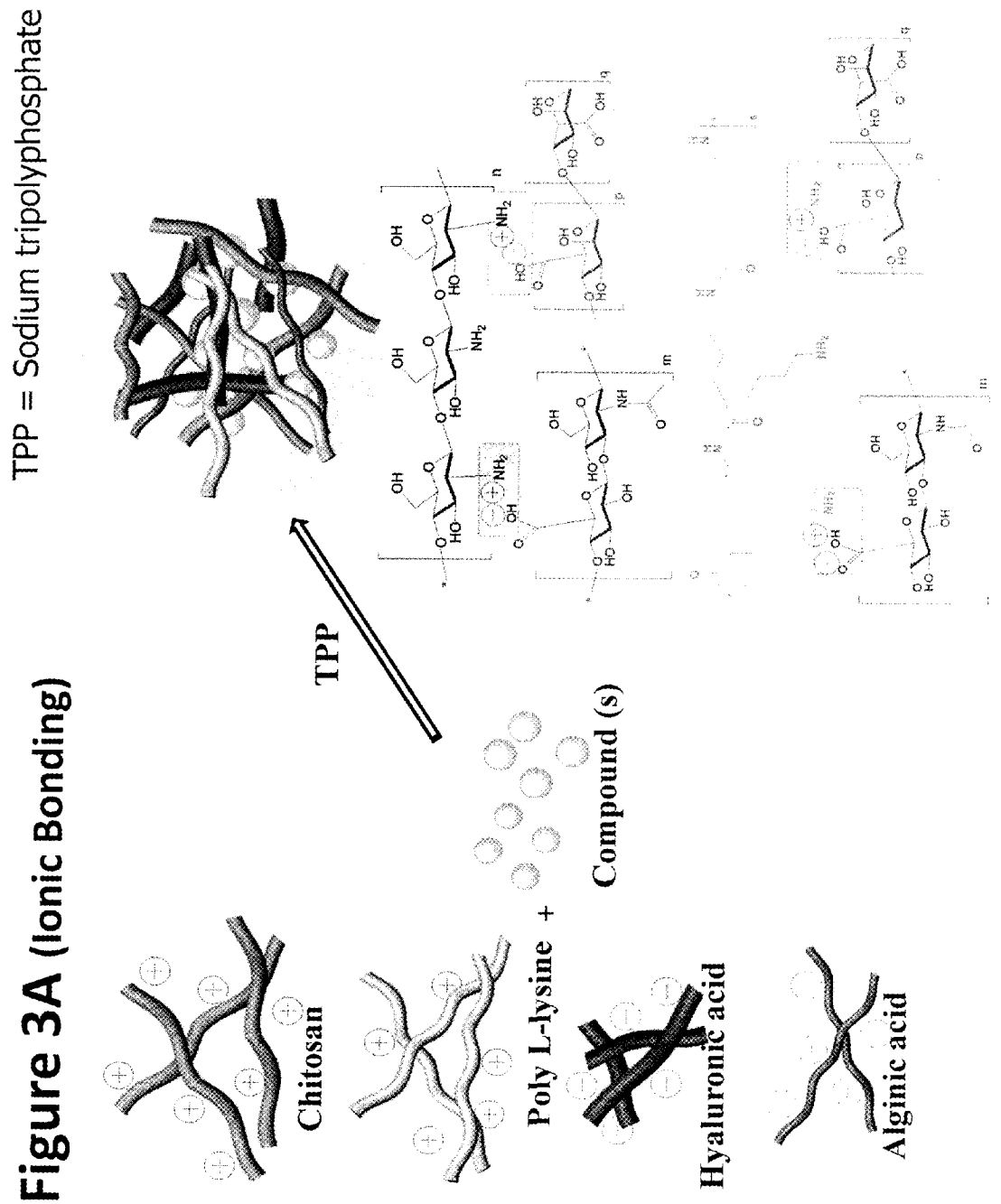

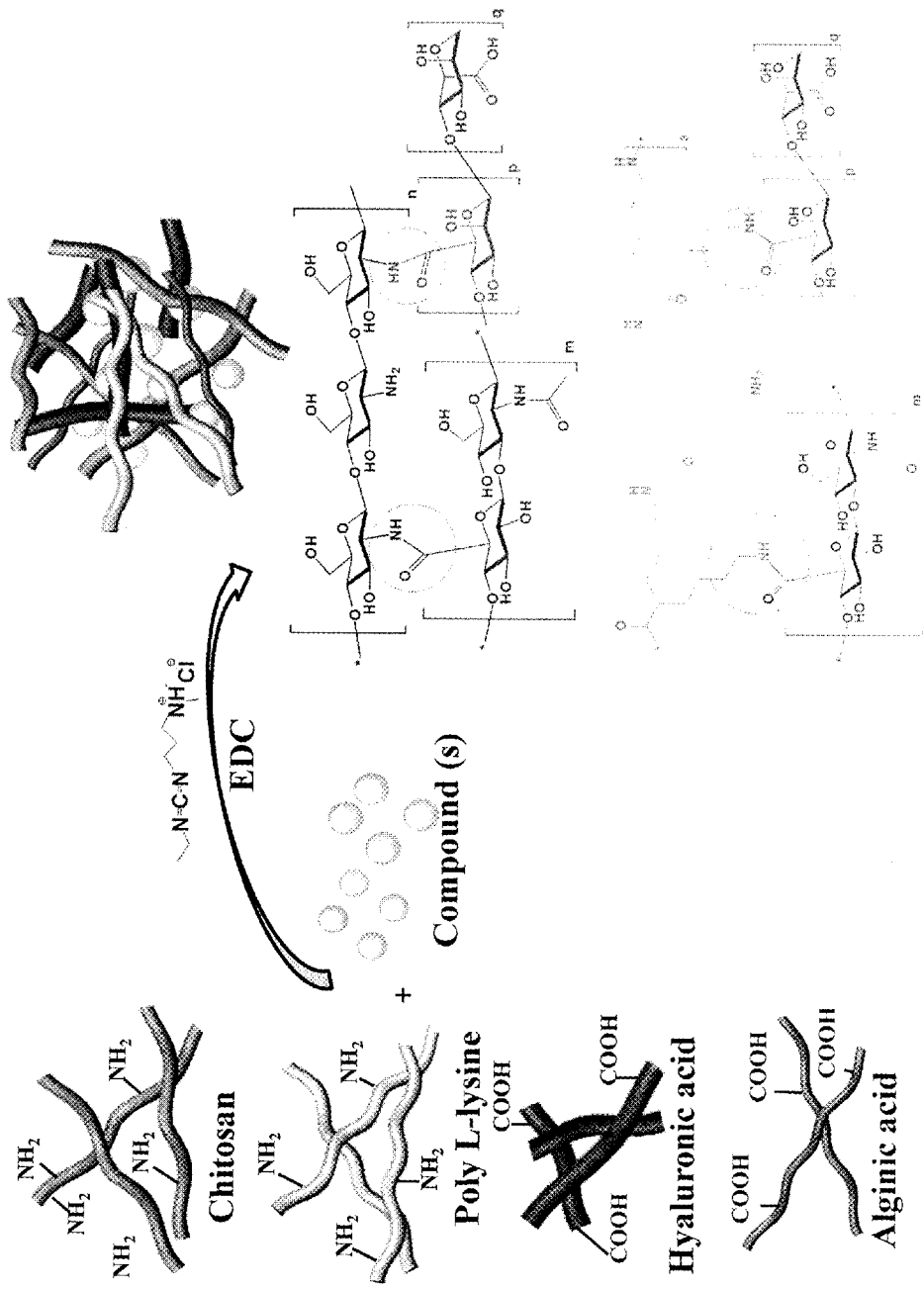

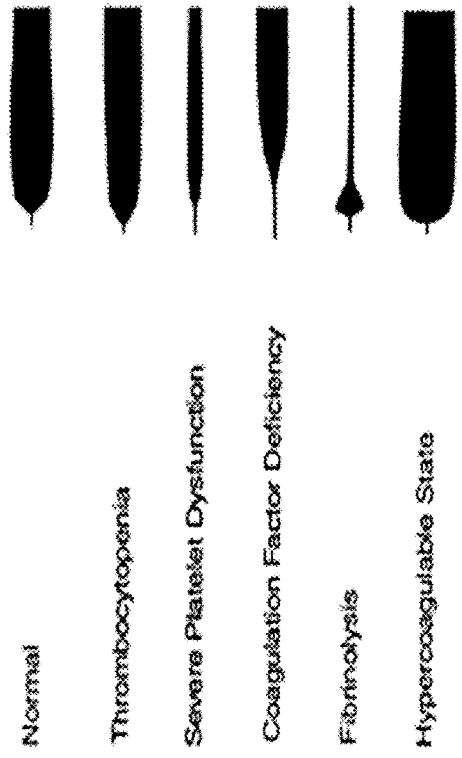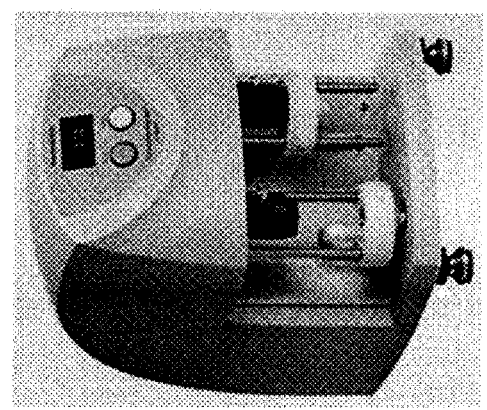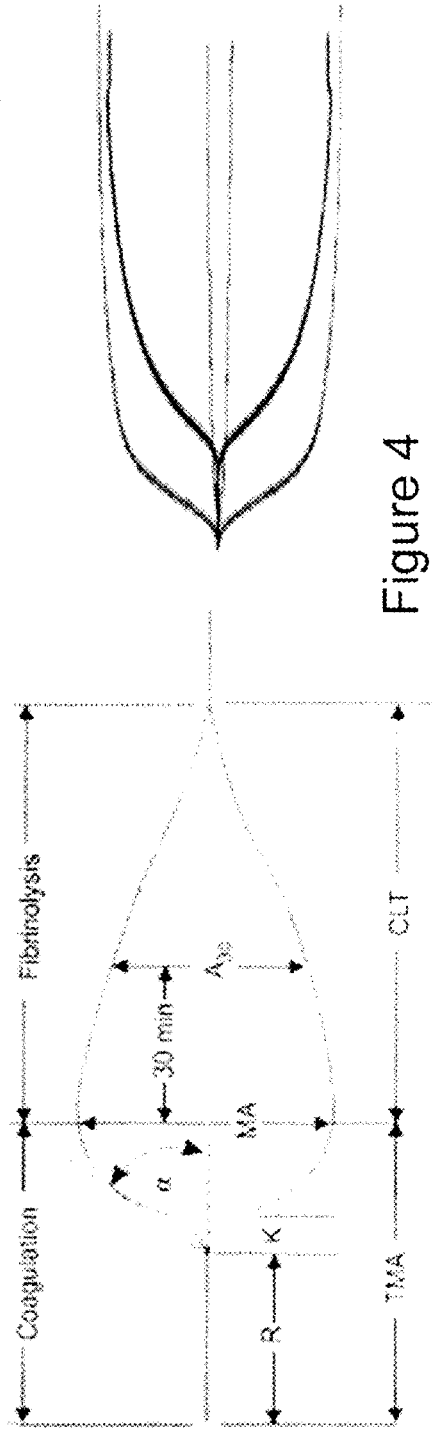
Figure 4

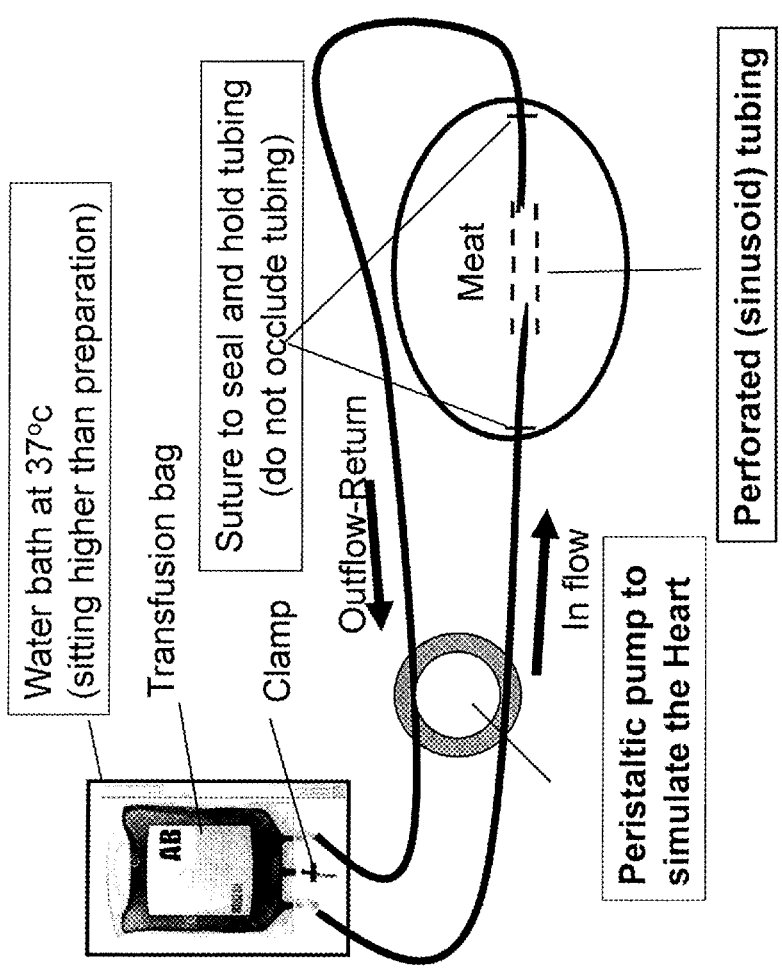
Figure 6: Sketch illustrating the simulation model system used to test the Hemostat V Seal (Micro-composite containing Transexamic acid, Thrombin, Calcium, Epinephrine and Cyanoacrylate

Figure 7: Effects of Matrix Composites on Human blood coagulation Kinetic
| Blood + Matrix Composite | R (Minutes) | MA (mm) |
| --- | --- | --- |
| Control | 12.8 | 58.6 |
| Chitosan/ Hyaluronic/ Alginic acid (M) | 7.8 | 63.5 |
| Poly-L Lysine/Hyaluronic/Alginic acid (M) | 5.9 | 64.0 |
| Chitosan/ Hyaluronic acid | 6.8 | 62.5 |
| Alginic acid/ Hyaluronic acid | 10.8 | 59.3 |

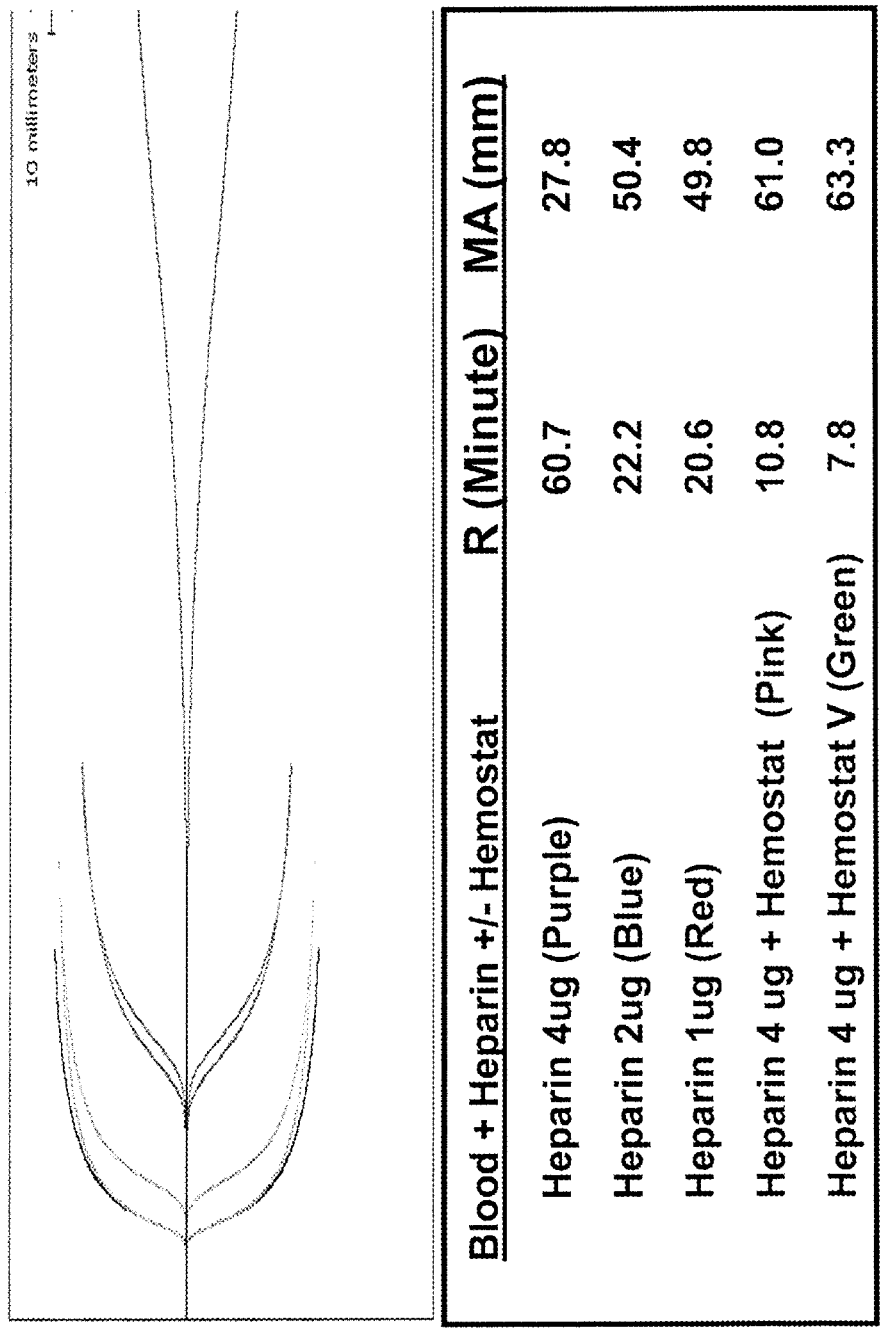
Figure 8: Effects of Hemostat V on Human Blood Coagulation kinetic
| Blood + Heparin +/- Hemostat | R (Minute) | MA (mm) |
|---|---|---|
| Heparin 4ug (Purple) | 60.7 | 27.8 |
| Heparin 2ug (Blue) | 22.2 | 50.4 |
| Heparin 1ug (Red) | 20.6 | 49.8 |
| Heparin 4 ug + Hemostat (Pink) | 10.8 | 61.0 |
| Heparin 4 ug + Hemostat V (Green) | 7.8 | 63.3 |

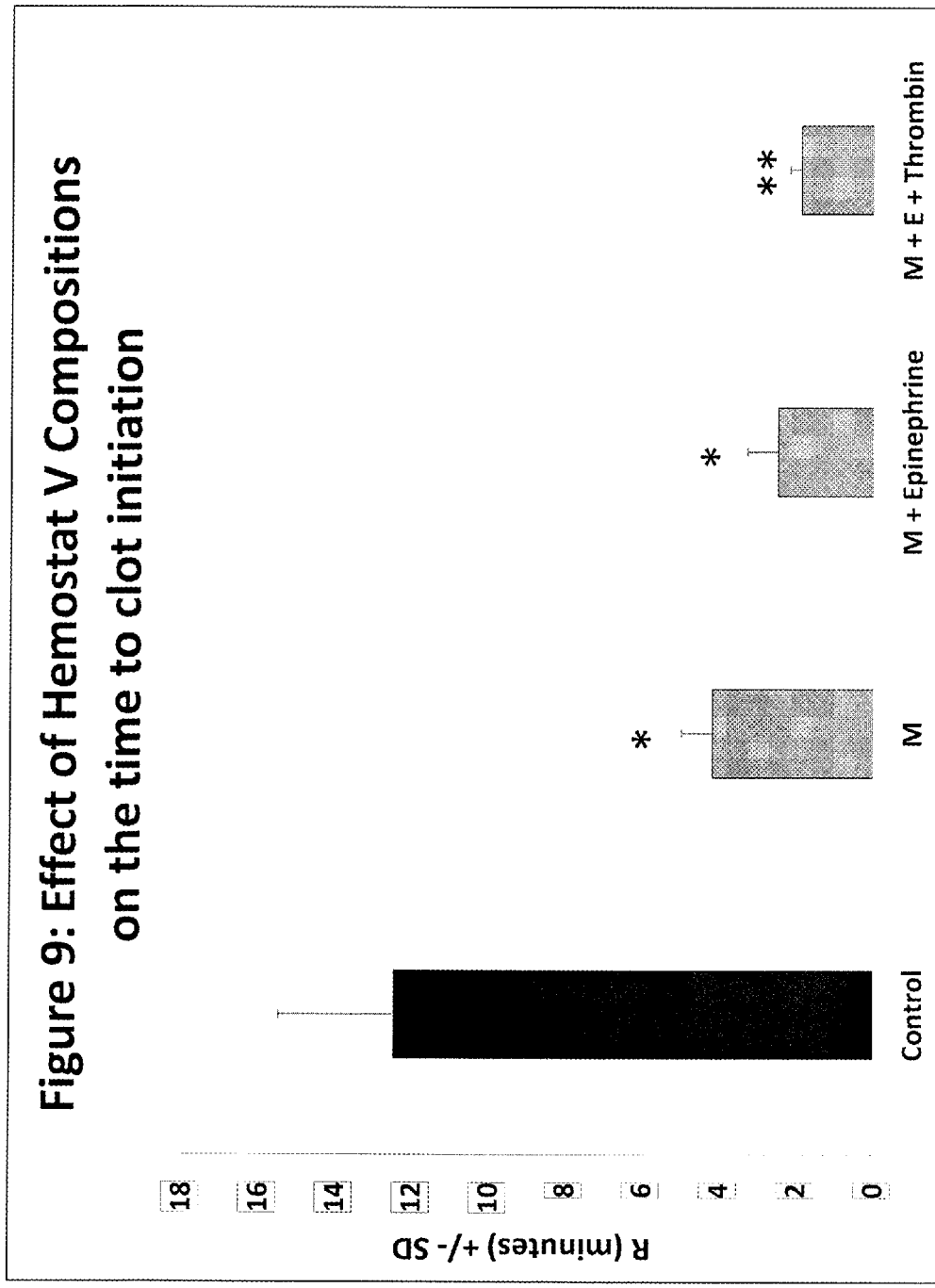

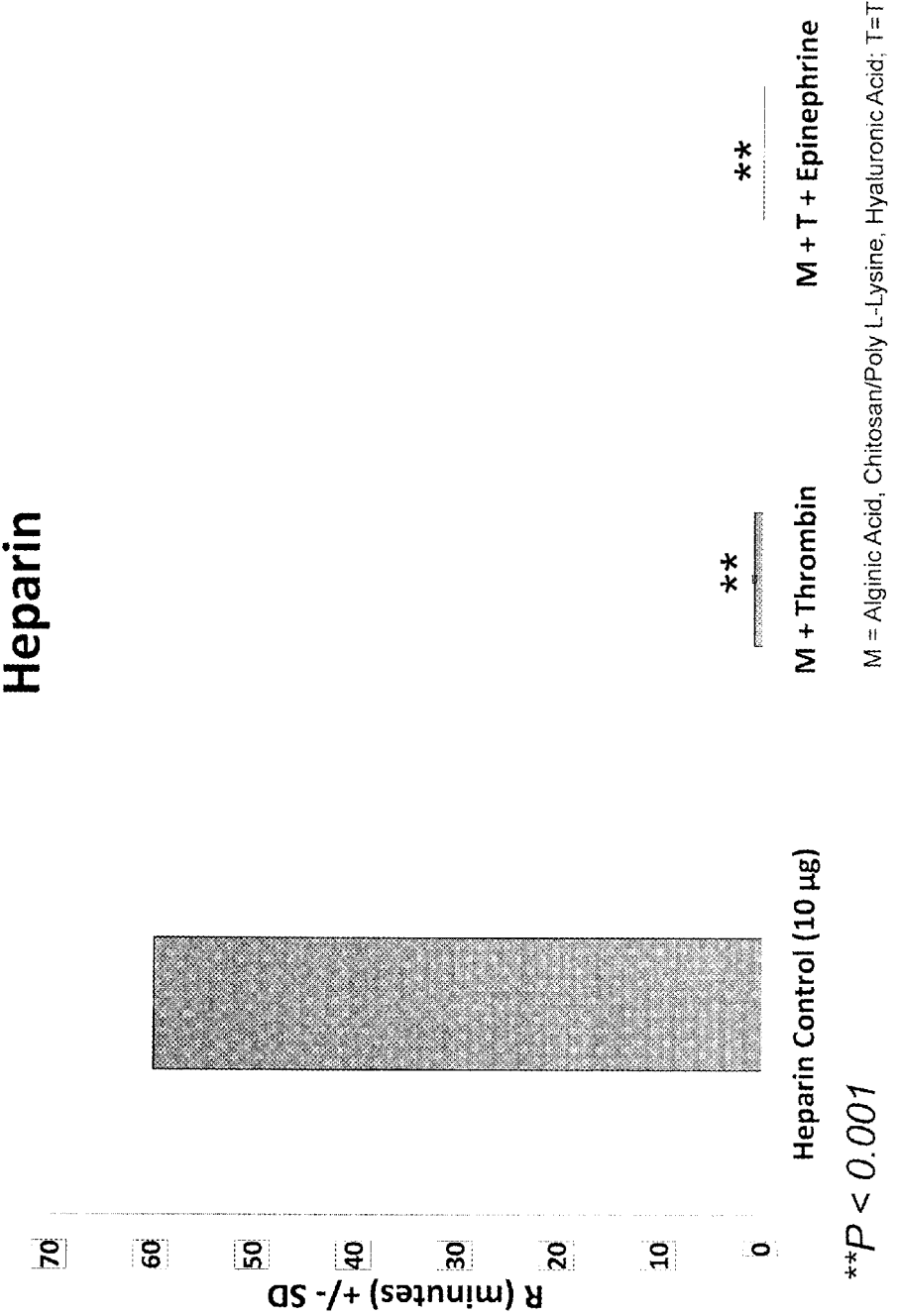

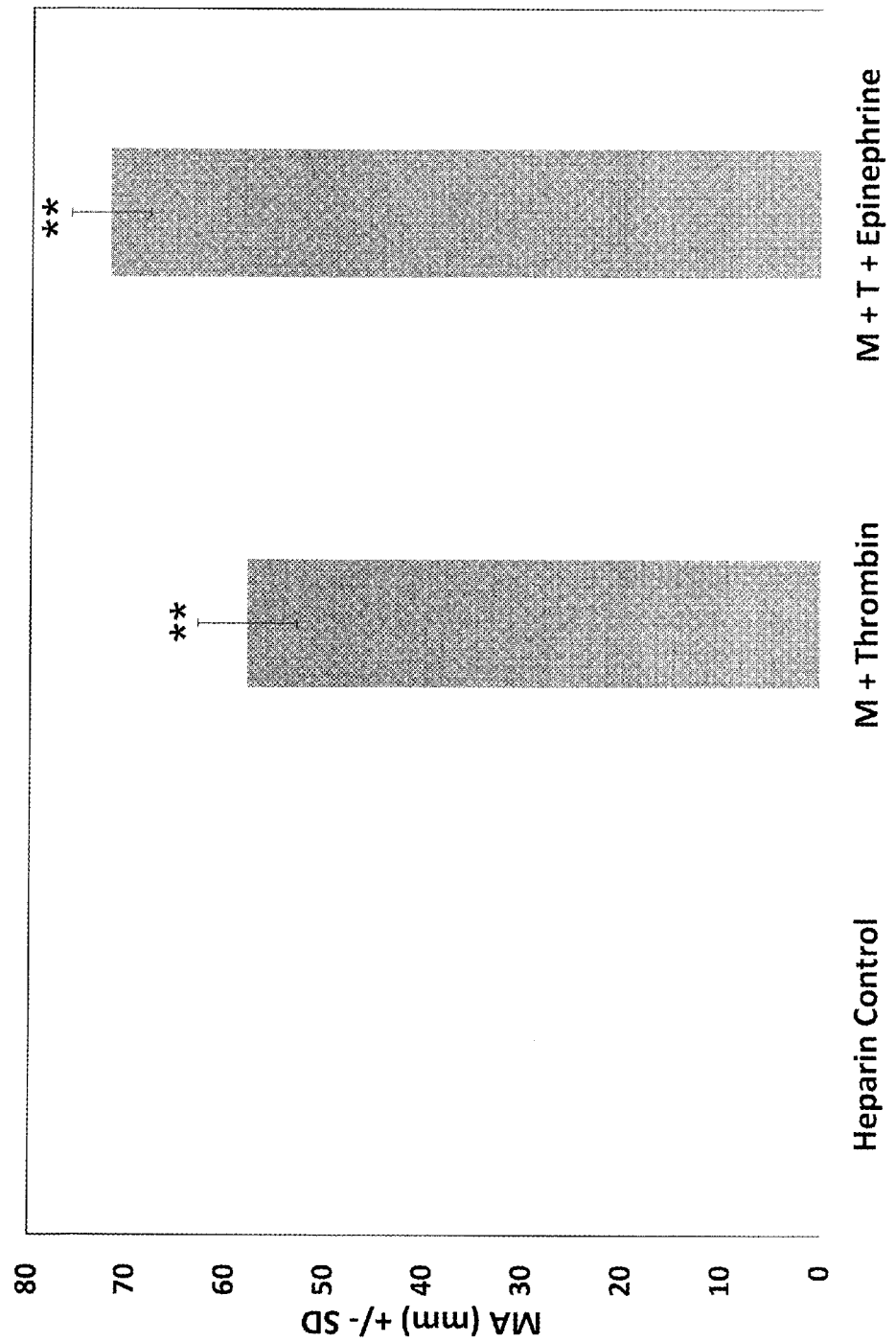

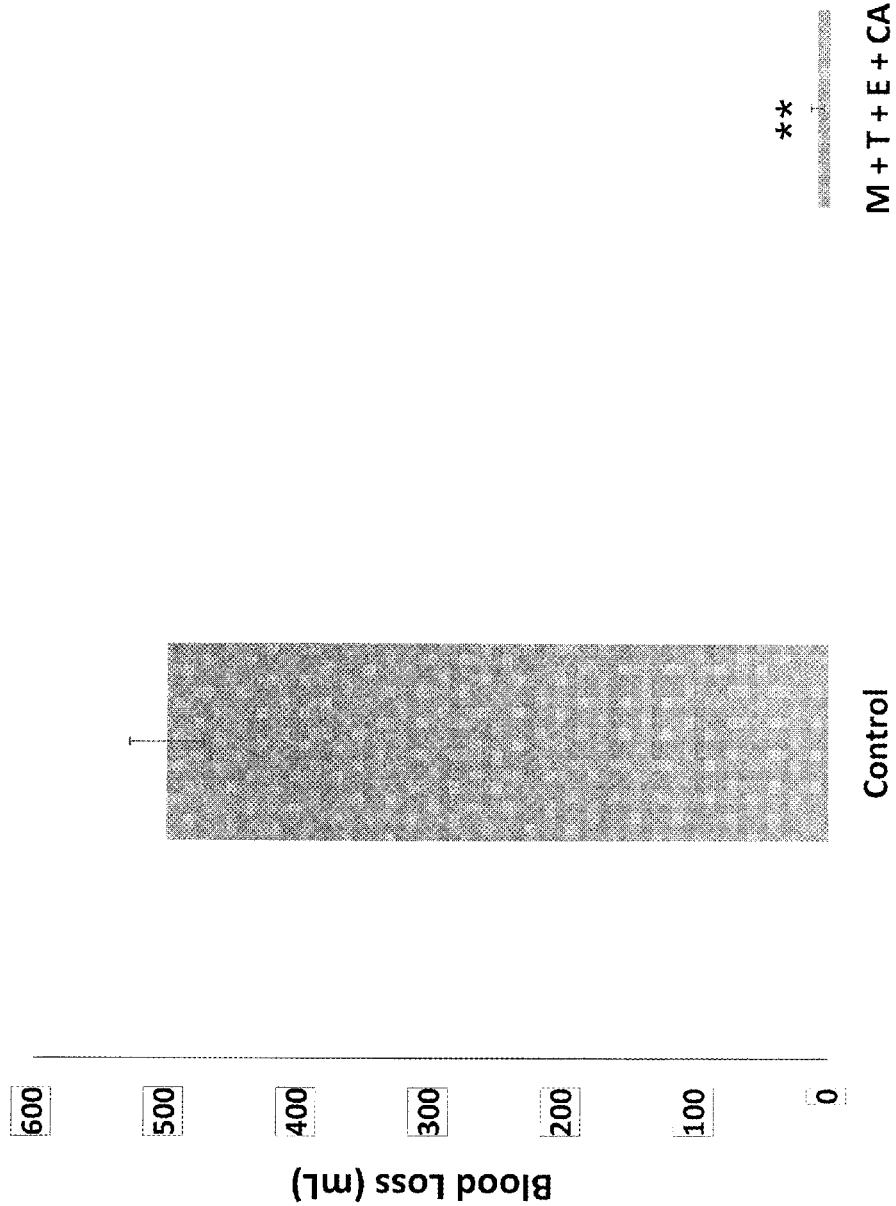

COMPOSITION AND METHOD FOR STOPPING HEMORRHAGE, INFECTION, AND ACCELERATING HEALING IN VARIOUS TYPES OF WOUND OR BURNS

RELATED APPLICATIONS

The present invention claims priority to U.S. Provisional No. 62/105,465, filed on Jan. 20, 2015, which is incorporated herein by reference in its entirety.

TECHNICAL FIELD

The present invention relates to a composition and associated method for use in surgery, bleeding, trauma, and treatment of burns, wounds and other injuries.

BACKGROUND

After a traumatic injury, hemorrhage is responsible for over 35% of pre-hospital deaths and over 40% of deaths within the first 24 hours (Kauvar, D. S., Lefering, R., and Wade, C. E. (2006), Impact of hemorrhage on trauma outcome: an overview of epidemiology, clinical presentations, and therapeutic considerations, *J Trauma* 60, 53-11), second only to the rates of death due to severe central nervous system injury. A cascade of medical problems (e.g., hemorrhage, impaired resuscitation, shock, inflammation and coagulopathy) may be life threatening, can begin with severe hemorrhage, and may occur simultaneously. The severity of each such problem is commonly associated with the extent of overall blood loss. Low blood pressure due to blood loss indicates immediate complications, including the incidence of multiple organ failure and life-threatening infections. See Heckbert, S. R., Vedder, N. B., Hoffman, W., Winn, R. K., Hudson, L. D., Jurkovich, G. J., Copass, M. K., Harlan, J. M., Rice, C. L., and Maier, R. V. (1998), Outcome after hemorrhagic shock in trauma patients. *J Trauma* 45, 545-549. See also, Franklin, G. A., Boaz, P. W., Spain, D. A., Lukan, J. K., Carrillo, E. H., and Richardson, J. D. (2000) Prehospital hypotension as a valid indicator of trauma team activation. *J Trauma* 48, 1034-1037; discussion 1037-1039.

Early trauma care focuses on minimizing hemorrhage and restoring circulation effectively.

Mitigation of battlefield injury and hemorrhage is a high priority of U.S. military trauma surgeons and researchers. There is no debate about the importance of hemorrhage control as a first-line measure by medics or emergency medicine personnel. While extremity wounds are more amenable to compression to stop bleeding, 15% of Operation Iraqi Freedom (OIF) and Operation Enduring Freedom (OEF) battle injuries are to the torso (chest, abdomen, pelvis and back), where compression cannot be applied. See Eastridge, B. (2009) Joint Theater Trauma Registry Data, September 2001-February 2008.

Non-compressible hemorrhage from truncal injury is the leading cause of potentially survivable deaths of American troops. See Kelly, J. F., Ritenour, A. E., McLaughlin D. F., Bagg, Apodaca, A. N., Mallak, C. T., Pearse, L., Lawnick, M. M., Champion, H. R., Wade, C. E., and Holcomb, J. B. (2008), Injury severity and causes of death from Operation Iraqi Freedom and Operation Enduring Freedom: 2003-2004 versus 2006. *J Trauma* 64, S21-26; discussion S26-27.

Patients who have penetrating wounds to the trunk are at risk of severe injuries to major vessels, causing massive hemorrhage, and are most likely to die during the acute (emergency) phase of care. Control of bleeding and limitation of blood loss is the only way to avoid the problems associated with massive hemorrhage in trauma.

Hemorrhagic shock is a severe and life-threatening condition. Over 21% of military casualties are in shock upon admission, and over 25% require a blood transfusion (Eastridge, B. (2009) Joint Theater Trauma Registry Data, June 2006-November 2009). Shock occurs when loss of blood leads to a lack of oxygen to the tissues, causing a systemic build-up of acids. In an attempt to reverse the acid build-up, the patient begins to hyperventilate and, along with other physiological changes, blood pressure increases and blood diverts from the renal system to the heart, lungs and brain. These symptoms occur due to the cellular response to the lack of oxygen, and lead to further breakdown and malfunction of cells, prompting various responses in the circulatory system.

If the problem is not treated or rectified, the cellular response will promote the dysfunction or complete failure of the vital organs, and the patient will die. Prevention of severe hemorrhage, or resuscitation with novel or advanced physiological resuscitation fluids, would diminish the onset of shock.

About 28% of patients with severe traumatic injury also have dysfunction in the process of coagulation (coagulopathy) when the patients arrive at the emergency department (MacLeod, J. B., Lynn, M., McKenney, M. G., Cohn, S. M., and Murtha, M. (2003), Early coagulopathy predicts mortality in trauma, *J Trauma* 55, 39-44). This dysfunction in the process of coagulation is often caused by dilution of the blood due to infusion of resuscitation products. Coagulopathy is associated with a 3.5- to 5-fold increase in mortality (MacLeod, J. B., Lynn, M., McKenney, M. G., Cohn, S. M., and Murtha, M. (2003), Early coagulopathy predicts mortality in trauma, J Trauma 55, 39-44); and Brohi, K., Cohen, M. J., and Davenport, R. A. (2007), Acute coagulopathy of trauma: mechanism, identification and effect, *Curr Opin Crit Care* 13, 680-685), and when combined with hypothermia and acidosis is known as the "lethal (or fatal) triad" because of the high likelihood of impending death.

Currently, there is no active intervention for non-compressible hemorrhage available to military or civilian medics and physicians; however, research of non-compressible hemorrhage control methods may offer solutions that could save lives.

Manufactured QuikClot® is an approved zeolite-based hemostatic agent for battlefield use. However, the exothermic reaction associated with QuikClot® as loose granules or as granules packaged in a mesh bag has potential burn effects at the site of application. Zeolites have hemostatic properties used to stop bleeding in severe hemorrhage. See Rhee P. Brown C, Martin M, Salim A. Plurad D, Green D, Chambers L, Demetriades D, Velmahos G, Alm H. (2008), QuikClot use in trauma for hemorrhage control: case series of 103 documented uses, J Trauma. 64(4):1093-9. See also, Arnaud F, Tomori T, Can W, McKeague A, Teranishi K, Prusaczyk K, McCarron R. (2008), Exothermic reaction in zeolite hemostatic dressings: QuikClot ACS and ACS+, Ann Biomed Eng. 36(10):1708-13.

It is widely accepted that severe bleeding is the leading cause of death from wounds on the battlefield, accounting for approximately over 50% of such deaths. It is estimated that one-third of these deaths could be prevented with enhanced hemorrhage control methods and devices. Such enhanced hemorrhage control would also prove very useful in non-military settings; e.g., hospitals and veterinary clinics, where hemorrhage is the second leading cause of death following trauma. No perfect solution currently exists for the effective treatment of excessive bleeding.

To date, application of continuous pressure with gauze bandage remains a primary intervention technique used to stem blood flow, especially flow from severely bleeding wounds. However, this continuous pressure with gauze bandage neither effectively nor safely stanches severe blood flow. This has been, and continues to be, a major survival problem in the case of severe life-threatening bleeding from a wound.

Furthermore, it is widely accepted that severe bleeding is the leading cause of death from wounds on the battlefield, accounting for approximately over 50 percent of such deaths. It is estimated that one-third of these deaths could be prevented with enhanced hemorrhage control methods and devices. Such enhanced hemorrhage control would also prove very useful in non-military settings; e.g., hospitals and veterinary clinics, where hemorrhage is the second leading cause of death following trauma.

Currently available hemostatic bandages such as collagen wound dressings or dry fibrin thrombin wound dressings are restricted to use in surgical applications, and are not sufficiently resistant to dissolution in high blood flow. These currently available hemostatic bandages also do not possess enough adhesive properties to serve any practical purpose. These currently available hemostatic bandages are also delicate and thus prone to failure should these hemostatic bandages be damaged by bending or loading with pressure. These hemostatic bandages are also susceptible to dissolution in hemorrhagic bleeding. Such dissolution and collapse of these hemostatic bandages can produce a loss of adhesion to the wound and allow bleeding to continue unabated.

It is generally accepted that hemostatic products for forward care in a battle zone must control bleeding quickly, be ready to use, be simple to apply, have a shelf life approaching two years, and prevent bacterial or viral transmission. The product's hemostatic action is time-critical in order to meet both military and civilian needs. Devices being investigated or used today as external methods of wound treatment range from absorbent pads containing clotting agents, pressure bandages, gauze, tourniquets for extremities, and trauma kits for wounds to the body.

A number of hemostatic products are available for treating wound trauma; for example, a bandage product using chitosan (deacetylated poly-N-acetyl glucosamine base, Hem Con Inc., Tigard, Oreg.), with limited shelf life and efficiency in stopping severe bleeding, Z-Medica Corporation, Wallingford, Conn., markets a pressure bandage product (QuikClot®) for use by U.S. troops. This product uses a granular, synthetic mineral zeolite to stop bleeding by adsorbing liquid and promoting clotting. However, QuikClot® generates heat that can cause burns if the bandage isn't applied correctly.

ActSys Medical Inc., Westlake Village, Calif., provides a hemostatic gauze product, ActCel®), which is a collagen-like natural substance created from chemically treated cellulose that expands 3-4 times its original size when in contact with blood, thus sealing off damaged vessels a d aiding clotting.

Medafor Inc., Minneapolis, Minn., sell a bio-inert, microporous polysaccharide macro-bead product that is synthesized from potatoes, called Trauma DEX®, which is a powdered micro-porous polymer product that stops bleeding by expanding at the wound site and dehydrating the blood, whereupon the body absorbs the material within 48 hours.

Another non-bandage approach employs a non-zeolite topical powder containing a hydrophilic polymer and potassium salt (Quick Relief, Sarasota, Fla.) which, after application, produces a flexible, protective scab to cover the wound site when the powder contacts the blood and slight pressure is applied.

No perfect solution currently exists for the effective treatment of excessive bleeding. Heat generation with respect to one type of agent is a major problem. The dressing's ability to adhere effectively when applied to deep wounds or wounds of irregular shape creates another major limitation. The ability to deal with excessive blood is another drawback, as is treatment and control of pressure bleeding from arterial bleeding.

Surgical and trauma wounds are the most common types of wounds addressed in the wound-care arena. Current bandages are made of gauze and are often applied in conjunction with an elastic bandage. The current bandages allow the wound to breath but are poor barriers to subsequent contamination. The current bandages cannot stop serious bleeding and require the application of pressure in the case of arterial bleeding. Conventional wound sealants fail to present an optimized combination of speed of clotting, effectiveness under pressure bleeding conditions, and clots that are dynamic over time in response to the needs of the trauma site. Typical wound sealants are usually used in conjunction with separate wound dressings. Clearly, surgical trauma caused by sharp objects occurs in a clean environment. However, trauma wounds not caused in a controlled environment are often intermediate sized, widespread, and dirty wounds with considerable tissue damage are found in road traffic accidents or on the battlefield.

Abrasions are generally caused by scraping of the skin's outer layer. Lacerations are jagged, irregular cuts or tears of the skin. Punctures are caused by an object piercing the skin layers, creating a small hole. Incisions are cuts commonly caused by knives or other sharp objects. Burns cause damage which may vary greatly in depth, size, and severity. Wounds due to firearms can be deep and with substantial tissue destruction. Dismemberment due to trauma requires immediate intervention to stop blood loss from the severed limb.

Liquid bandage formulations are available to the Over-the-Counter (OTC) consumer market. Liquid bandage preparations are often used for covering and protecting minor lacerations and abrasions, friction blisters and paper cuts. When applied to the skin, the solution in a liquid bandage evaporates to form a protective film over the application area and to promote healing. The polymerized film covering creates a moist wound healing environment to increase wound healing compared with conventional dressings. Most liquid bandage preparations claim to stop minor bleeding, create a protective seal over the wound, keep out water, dirt and germs, and generally act as a mechanical barrier to common microbial organisms and other forms of contamination. Liquid bandage produces are available from numerous commercial sources. Powder-based hemostats are also widely available OTC.

Cellulose products which are used include microcrystalline cellulose (Avicel range), methylcellulose, carboxymethyl cellulose, and other materials such as cross-linked polyvinyl pyrrolidone (PVP), used singly or in admixture. Also, suitable carriers include polyethylene glycol (PEG), in one embodiment having a molecular weight of about 1000; polyvinyl pyrrolidone (PVP), in one embodiment having an average molecular weight of about 50,000; Poly(acrylic acid), PVA, Poly (methyl vinyl ether co-maleic anhydride), Poly (ethylene oxide), and dextran, typically having an average molecular weight of about 40,000.

Shellfish derived chitosan was used in chitosan dressings. For example, U.S. Pat. No. 4,394,373 employs chitosan in liquid or powder form to agglutinate blood in microgram/mL quantities.

U.S. Pat. No. 4,452,785 is directed to a method of occluding blood vessels therapeutically by injecting chitosan directly into the vessels.

U.S. Pat. No. 4,532,134 relates to hemostasis, inhibiting fibroplasias, and promoting tissue regeneration by placing in contact with the tissue wound a chitosan solution or water-soluble chitosan. The chitosan forms a coagulum, which prevents bleeding.

U.S. Pat. No. 5,700,476 describes collagen based structurally inhomogeneous sponges for wound dressings and/or implant applications formed by freeze drying techniques employing at least one pharmacological agent and at least one substructure.

U.S. Pat. No. 2,610,625 relates to freeze dried sponge structures that are highly effective in stopping the flow of blood or other fluids and which will be absorbed after a time in the body.

U.S. Pat. No. 5,858,350, relates to a process to make diatom derived biomedical grade, high purity chitin and chitin derivatives.

BRIEF SUMMARY

The present invention provides a composition and a method of applying the composition to a site on or within a body of a mammal. The composition comprises a hydrogel matrix that includes at least one polymer cross linked, via ionic or covalent bonding, with both hyaluronic acid and alginic acid. The at least one polymer is chitosan, poly L-Lysine, or a combination thereof.

BRIEF DESCRIPTION OF THE DRAWINGS

FIG. 1A depicts synthesis of a hydrogel matrix, said hydrogel matrix comprising chitosan ionically bonded to both hyaluronic acid and alginic acid, said hydrogel matrix encapsulating various compounds, in accordance with embodiments of the present invention.

FIG. 1B depicts synthesis of a hydrogel matrix, said hydrogel matrix comprising chitosan covalently bonded to both hyaluronic acid and alginic acid, said hydrogel matrix encapsulating various compounds, in accordance with embodiments of the present invention.

FIG. 2A depicts synthesis of a hydrogel matrix, said hydrogel matrix comprising poly L-Lysine ionically bonded to both hyaluronic acid and alginic acid, said hydrogel matrix encapsulating various compounds, in accordance with embodiments of the present invention.

FIG. 2B depicts synthesis of a hydrogel matrix, said hydrogel matrix comprising poly L-Lysine covalently bonded to both hyaluronic acid and alginic acid, said hydrogel matrix encapsulating various compounds, in accordance with embodiments of the present invention.

FIG. 3A depicts synthesis of a hydrogel matrix, said hydrogel matrix comprising chitosan and poly L-Lysine ionically bonded to both hyaluronic acid and alginic acid, said hydrogel matrix encapsulating various compounds, in accordance with embodiments of the present invention.

FIG. 3B depicts synthesis of a hydrogel matrix, said hydrogel matrix comprising chitosan and poly L-Lysine covalently bonded to both hyaluronic acid and alginic acid, said hydrogel matrix encapsulating various compounds, in accordance with embodiments of the present invention.

FIG. 4 depicts a representative tracing by a Thrombelastography (TEG) system used in the current study, in accordance with embodiments of the present invention.

FIG. 6 depicts use of a simulation model system, in accordance with embodiments of the present invention.

FIG. 7 illustrates the effect of matrix composites on human blood coagulation kinetics, in accordance with embodiments of the present invention.

FIG. 8 depicts the effect of Hemostat and Hemostat V composition on clot initiation kinetic (R) and clot strength (MA), in accordance with embodiments of the present invention.

FIG. 9 depicts the effect of Hemostat V on reversing time to clot initiation, in accordance with embodiments of the present invention.

FIG. 10 depicts the effect of Hemostat V composition on time to clot for blood loss in severe hemorrhage simulation model with heparin as a control, in accordance with embodiments of the present invention.

FIG. 11 depicts the effect of Hemostat V composition on clots strength with heparin as a control, in accordance with embodiments of the present invention.

FIG. 12 depicts the effect of Hemostat V Seal on blood loss in simulation model, in accordance with embodiments of the present invention.

DETAILED DESCRIPTION

Figure 5:
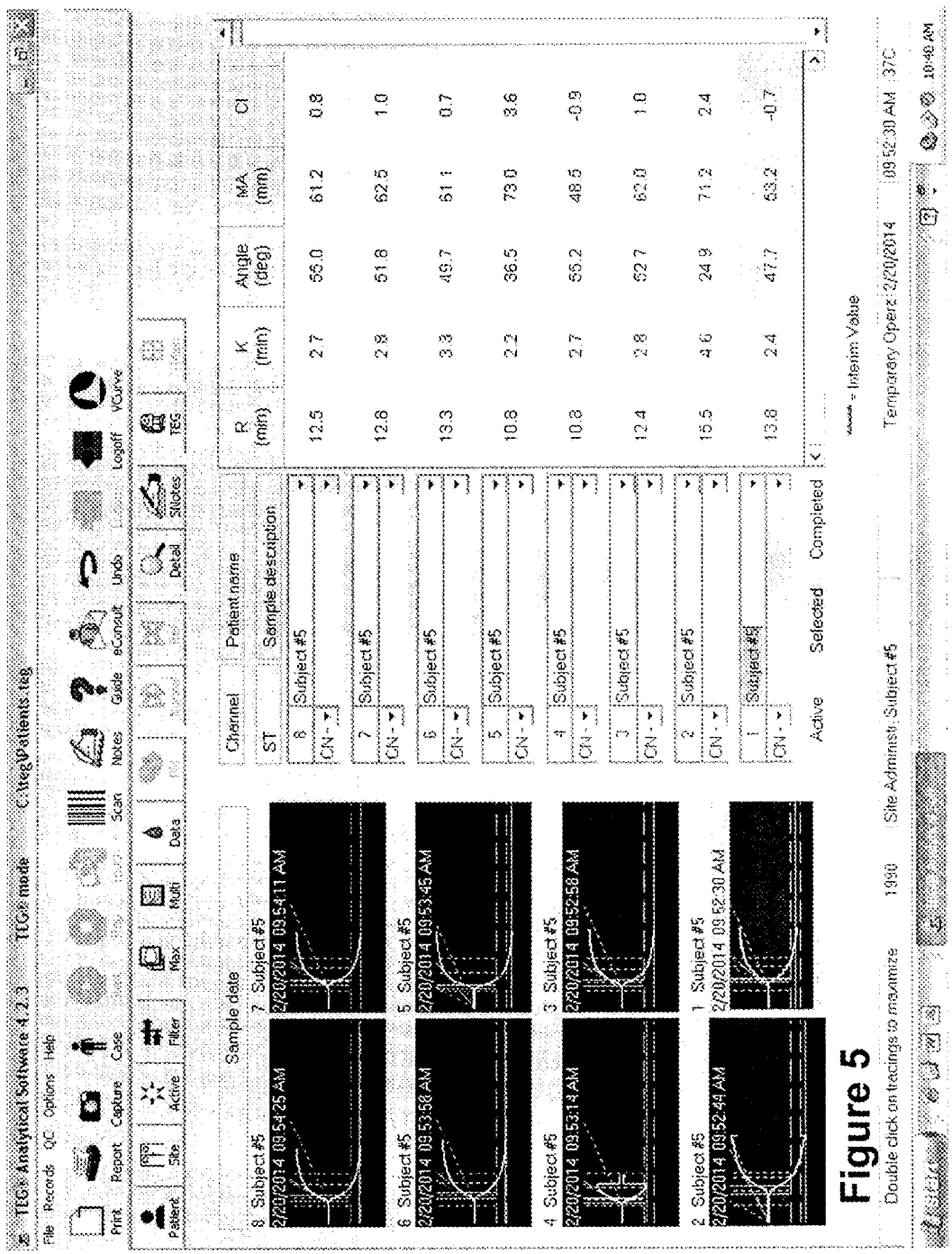
FIG. 5 depicts representative clot kinetic parameters and tracings for blood obtained from the same subject, in accordance with embodiments of the present invention.

The preset invention is directed to hemorrhage control wound dressings, and methods of using and producing such dressings. The subject wound dressing is constructed from a non-mammalian material for the control of severe bleeding.

The present invention provides a nano-scale or micro-scale composition that includes a matrix (M) comprising a first polymer component cross linked with a second polymer component to form a hydrogel. A polymer component is defined as one or more polymers. The nano-scale or micro-scale of the composition is a linear size of the matrix. The first and second polymer components are cross linked via ionic bonding or covalent bonding. The first polymer component is polycatioinic chitosan or polycatioinic Poly L-Lysine. The second polymer component is hyaluronic acid and alginic acid. The nano-scale of the composition encompasses a range of 100 nm to less that 1000 nm. The micro-scale the composition encompasses a range of 1 µm to 10 µm. The hydrogel may comprise tranexamic acid, calcium salt (e.g., calcium chloride: $CaCl_2$) with or without Kaolin, thrombin, epinephrine or norepinephrine (each functions as a vasoconstrictor), and sealant (Cyanoacrylate) for stopping hemorrhage, infections, pain relief, and accelerating wound healing in various types of bleeding episodes and burns. The nano or micro formulations can also be used as a slow-release device or drug-delivery vehicle for growth factors, antibiotics, and local anesthetics to improve wound healing, prevent or treat infection, and relieve pain. The hydrogel polycatioinic matrix composites contain combinations of intrinsic and extrinsic coagulation pathways activators along with platelet activator, vasoconstrictor, and antifibrinolytic for immediate stopping of hemorrhage or fatal bleeding.

The nano to micro-composites may be formulated as a dry powder, spray, gel, bandage, gauze mixed with honey along with 2-octyl cyanoacrylate, which provides skin adhesive as a sutureless surgery solution. This novel composition can be fitted to any size or shape wound, including penetrating or surgical wounds or burns for human or veterinary utilities along with 2-octyl cyanoacrylate. The wound dressing for controlling severe bleeding is formed of a biomaterial comprising chitosan/poly L-Lysine, a hydrophilic polymer, a polyacrylic polymer, or a combination thereof. The kind of severe, life-threatening bleeding contemplated by this invention is typically of the type capable of being stanched when a conventional gauze wound dressing is applied with conventional pressure to the subject wound. The wound dressing of the present invention is capable of stopping life-threatening bleeding from a wound by adhering to the wound site, sealing the wound, accelerating blood clot formation at the wound site, and preventing bleed out from the wound site.

In one embodiment, a method applies the nano-scale or micro-scale composition to a site on or within a body of a mammal. In one embodiment, the mammal is a human being. In one embodiment, the composition is applied to the site when the mammal is bleeding at the site, wherein the composition is configured to reduce a time to initiate formation of a clot formed at the site, and to increase a clot strength of the clot, relative to a control of nothing being administered at the site to stop the bleeding.

The present invention relates to a dry powder or liquid fibrin sealant, sponge, spray for use in surgery, trauma and other wounds or injuries. The present invention further relates to novel nano to micro composites comprising dry powder fibrin sealant for use in the treatment of wounds or injuries, in particular for use as a topical hemostatic composition as a device as well as a therapeutics for immediate stopping of bleeding, prevention of infection and acceleration of wound healing. The nano to micro composites can be formulated as a dry powder, spray, gel, bandage, gauze mixed with honey. This novel composition can be fitted to any size or shape wound, including penetrating or surgical wounds or burns.

Different hydrogel polycatioinic matrix (Chitosan and/or Poly L-Lysine micro-composites (containing intrinsic, extrinsic coagulation pathways, and platelet activators in accelerating blood platelet-fibrin clotting) have been evaluated using standard global coagulation assay, namely Thrombelastography, using human total of 5 ml blood from human volunteers. Additionally, the efficiency of the optimal hydrogel compositions that have the shortest Time to Clotting (R) and the strongest clot strength (MA) were evaluated in stopping severe bleeding in a hemorrhage simulation model.

Polycatioinic chitosan/Poly L-Lysine interacts directly, via a dual mechanism, with negatively charged platelets (thrombocytes and red blood cells (erythrocytes), and rapidly absorbs fluids. This dual mechanism forms a cross-linked pseudo-clot (pseudo-thrombus), which adheres to tissue and plugs the bleeding site. Chitosan/Poly L-Lysine do not initiate the normal clotting cascade and do not result in clots being formed at the bleeding site.

A wound dressing, prepared in accordance with the present invention, for control of severe, life-threatening bleeding may have some or all of the following properties: i) easily and quickly applied in one step after removal from package; ii) rapid and strong blood clotting; iii) rapid and strong tissue adhesion; iv) internal cohesive properties; v) rapid and strong wound sealing; vi) resistant to dissolution under strong blood flow; vii) good compliance with the injury; viii) good mechanical seating of bandage on tissue to stop slipping by controlled tissue contacting surface-texture; ix) ability to be treated roughly without compromising efficacy; (x) capability to close wound without the need for suture; (xi) capability to prevent wound infection; (xii) capability to accelerate wound healing; and (xiii) capability to provide relief of pain.

The nano to micro-composite of the present invention forms rapid blood clots after blast trauma such as experienced by soldiers exposed to severe bomb blasts or victims in car accidents. Nano-scale encompasses a range of 100 nm to less than 1000 nm, and micro-scale scale encompasses a range from 1 to 100 µm, via ionic or covalent bonding in hydrogel containing thrombin, tranexamic acid, calcium salt with or without zeolite or kaolin, epinephrine or norepinephrine (vasoconstrictor), and Extracellular Matrix Proteins (Hydrogel), for stopping bleeding, infections and accelerating wound healing in various types of bleeding episodes and burns.

Non-biologically active agents can also be incorporated into the hydrogel matrix. For example, polysaccharide thickeners such as hydroxyethyl cellulose, carboxymethyl cellulose, gum, gelling agents, locust bean gum, xanthan gum and the like, polymer thickeners such as polyacrylic acids and copolymers, polyacrylamides and copolymers, alcohols, maleic anhydride copolymers and the like can be added to produce a stiffer hydrogel.

Polysaccharide or honey thickeners may also be added to the aqueous solutions of the polymer components to ensure that the solutions are of suitable viscosity for application. For example, if the hydrogel is to be formed in situ on a target area such as a wound or tissue, the aqueous solutions of the polymer components should be sufficiently viscous along with 2-octyl cyanoacrylate, which provides skin adhesive as a sutureless surgery solution.

The ability of the hydrogels to reduce both bleeding and adhesions, makes the hydrogels a valuable tool in practically any surgical procedure. Examples of surgical procedures in which the hydrogels of the present invention can be used include, but are not limited to, abdominal procedures such as bowel surgery, thoracic procedures, orthopaedics procedures such as division of adhesions on flexor and extensor tendons, and burns procedures.

The present invention also provides wound dressings capable of releasing a hydrogel of the invention when moistened. The wound dressing can be any suitable dressing known in the art such as, inter aria, bandages, strips, pads, gauzes, films, spray, stockings and tape.

When the wound dressing is moistened, the first and second polymer components cross-link, via ionic or covalent bonding, and form a hydrogel in the aqueous component of the wound dressing. The wound dressing can be moistened either by external fluid containing fibrinogen to be applied immediately following the described composite containing alpha or gamma human or bovine thrombin. The rate at which the hydrogel forms can be altered by altering the component polymers. Different applications of the wound dressing may require different rates of hydrogel formation.

The present invention provides nano-scale to micro-scale hydrogel composites containing alpha or gamma human or bovine thrombin, tranexamic acid, calcium sulfate with or without Zeolite or Kaolin, epinephrine or norepinephrine vasoconstrictor, and Extracellular Matrix Proteins for stopping bleeding, antibiotics against infections and growth factors for acceleration of wound healing in various types of bleeding episodes and burns.

The wound dressing may contain additional agents such as antiseptics and other biologically active agents, as discussed above. These agents can be incorporated into the dressing materials using standard methods known in the art, or may be incorporated into the polymer solutions that are blended into the structure of the dressing along with 2-octyl cyanoacrylate which provides skin adhesive as a sutureless surgery solution.

The present invention provides new techniques, devices, and drugs for bleeding and/or hemorrhage control. Despite all of the technology currently available, bleeding and hemorrhage control is still a major unresolved problem in emergency medical care. Almost 50% of all deaths in the first 48 hours of hospitalization are related to an inability to adequately control bleeding. Failure to stop bleeding within the first hours is almost always fatal, especially when multiple trauma sites are involved.

Gums and gelling agents that can be used include, for example, tragacanth, karaya gum, soluble starch, gelatin, pectin, guar gum and gellan gum. A particularly useful additive is Emdex®; i.e., a hydrated form of dextrates (spray crystallized dextrose containing small amounts of starch oligosaccharides). The fibrin functions as a sealant that will appear as a stable foam once fully reacted and the clot has formed.

Another embodiment of the present invention provides a liquid hemostatic composition for topical delivery on minor abrasions, cuts, scrapes, scratches, burns, sunburns, ulcers, internal venous bleeding, external venous bleeding, and surgical trauma, with the composition comprising the fibrin sealant powder composition in a non-aqueous liquid carrier for forming a thin-film barrier over the site of injury. The formulation may be easily applied to the wound site in variable quantities and will quickly stop bleeding.

The present invention also comprises a process for preparing a viscous water soluble fibrin sealant paste, salve, and ointment or suspension composition, the process comprising the steps of: admixing the fibrin sealant powder composition of the present invention and polyethylene glycol. Such suspensions may optionally include a surfactant, or other suitable suspending agent, to prevent flocculation. In one embodiment, the nano to micro scale composition contains 50-60% chitosan/Poly L-Lysine, 10% alginic acid, 20-30% hyaluronic acid, with composition's molecular weight ranging from 4,000-8,000 Dalton. In one embodiment, the chitosan/Poly L-Lysine has a weight average molecular weight of at least about 60-150 kDa, with 25-40% acetylation. In one embodiment, the chitosan/Poly L-Lysine has a viscosity at 25° C. in a 1% solution of acetic acid of about 200-2000 centipoise. In one embodiment, the inventive composition includes chitosan/Poly L-Lysine nano (100 to less than 1000 nm) to micro (1-10 µm)-particles with zeta potential off 10 to +30 mV, thrombin, tranexamic acid, calcium salt with or without Zeolite or Kaolin, epinephrine or norepinephrine (vasoconstrictor), Extracellular Matrix Proteins (Matrigel®) for stopping bleeding, infections and accelerating wound healing in various types of bleeding episodes and burns and 2-octyl cyanoacrylate which provides skin adhesive as a sutureless surgery solution.

In one embodiment, the present invention provides a process for preparing a compressed composite sponge or spray for hemorrhage control. The process comprises: (a) degassing chitosan/Poly L-Lysine biomaterial solution by heating the chitosan/Poly L-Lysine biomaterial solution and applying a vacuum; (b) freezing the chitosan/Poly L-Lysine-Hyaluronic-alginic ionically or covalently bonded with SNACH biomaterial solution containing calcium salt with or without Zeolite or Kaolin, epinephrine or norepinephrine (vasoconstrictor), (c) adding Extracellular Matrix Proteins; (d) compressing the composition to obtain a compressed sponge; and (e) sterilizing the compressed sponge. In one embodiment, the compressed sponge is sterilized by gamma irradiation or an electron beam (i.e., E beam).

In one embodiment, a paste, salve, or ointment or suspension composition may also be used in conjunction with, for example, a gelatin sponge, gauze or collagen material by either coating such material as a substrate with the composition listed above and applying the coated material to the hemorrhaging site or first applying the composition to a hemorrhaging site and placing the gelatin sponge, gauze or collagen on top of the composition and applying pressure thereto. The paste, salve, or ointment of the present invention has a viscosity and potency which is high enough to permit a hemostatic effective use of the paste, salve, or ointment by a surgeon by dipping of a gloved finger into the paste, salve, or ointment and placing the paste salve, or ointment over the bleeding site. This paste salve, or ointment is water soluble, and sufficiently yielding to spread readily on tissue or skin.

The aerosol package of the present invention may be prepared and handled in such manner that the contents of the aerosol package will be sterile when sprayed. The use of bacterial filters and aseptic processing techniques results in a sterile product.

In another embodiment, a local anesthetic (e.g., Lidocaine) along with a neovascularization agent may be added into the above nano or micro composition.

The inventive composition may be applied locally for pain relief and promotion of neovascularization to enhance healing of nerve and tissue.

A drug comprising the inventive composition could elute over time after placement into the involved anatomic site, which would represent advancement over the present manner of drug delivery and take advantage of longer pain free episodes to allow for a more typical routine of activities as well as allow for an opportunity to build surrounding structural support.

The compressed sponge of the present invention may further comprise an active ingredient. The active ingredient may include, but is not limited to, calcium, thrombin, factor VIIa, factor XIIIa, penicillin, ampicillin, methicillin, amoxicillin, clavamox, clavulanic acid, aztreonam, imipenem, streptomycin, Kanamycin, Tobramycin, gentamicin, vancomycin, clindamycin, erythromycin, polymyxin, bacitracin, amphotericin, nystatin, rifampicin, tetracycline, doxycycline, chloramphenicol, or combinations thereof.

In one embodiment, the compressed composite sponge for hemorrhage control comprises a hydrophilic polymer sponge and a wettable polymer matrix or wettable polymer matrices inside the sponge and/or at the sponge surface. The hydrophilic polymer sponge may include alginate, a hydrophilic polyamine, a chitosan/Poly L-Lysine derivative, poly Lysine, polyethylene imine, xanthan, carrageenan, quaternary ammonium polymer, chondroitin sulfate, a starch, a modified cellulosic polymer, a dextran, hyaluronan or combinations thereof.

The wettable polymer may include non-woven mats, woven mats, molded polymer mesh and low density sponges. The wettable polymer may include, but is not limited to, a chitin, an alginate, a neutralized chitosan, a re-acetylated chitosan, poly(glycolic acid), a poly(lactic acid), a poly(e-caprolactone), a poly(β-hydroxybutyric acid), a poly(β-hydroxyvaleric acid), a polydioxanone, a poly(ethylene oxide), a poly(malic acid), a poly(tartronic acid), a polyphosphazene, a polyethylene, a polypropylene, a metallocene polymer, a polyurethane, a polyvinylchloride polymer, a polyester, a polyamide, or combinations thereof. In one embodiment, the hydrophilic polymer is chitosan and/or Poly L-Lysine.

In one embodiment, the chitosan/Poly L-Lysine has a weight average molecular weight of at least about 60-100 kDa. In one embodiment, the chitosan has a weight average molecular weight of at least about 110-150 kDa. In one embodiment, the chitosan has a viscosity, at 25° C. in a 1% solution of acetic acid, of about 100 centipoise to about 2000 centipoise. In one embodiment, the chitosan has a viscosity, at 25° C. in a 1% solution of acetic acid (AA), of about 125 centipoise a about 1000 centipoise.

The compressed sponge may comprise a textile thread impregnated with a hydrophilic polymer. The textile thread is impregnated with a hydrophilic polymer. In one embodiment, the hydrophilic polymer is chitosan. The hydrophilic polymer may also include, but is not limited to an alginate, a hydrophilic polyamine, a chitosan derivative, poly L-lysine, polyethylene imine, xanthan, carrageenan, quaternary ammonium polymer, chondroitin sulfate, a starch, a modified cellulosic polymer, a dextran, hyaluronic, or combinations thereof. The starch may include amylase, amylopectin, or a combination of both amylopectin and amylase.

The compressed composite sponge may further comprise a backing support layer. The backing support layer may be a layer of polymeric material. The polymeric material may be a synthetic non-biodegradable material or a naturally occurring biodegradable polymer. The synthetic biodegradable materials may include poly(glycolic acid), poly(lactic acid), poly(e-caprolactone), poly(.beta.-hydroxybutyric acid), poly-hydroxyvaleric acid), polydioxanone, poly(ethylene oxide), poly(malic acid), poly(tartronic acid), polyphosphazene, copolymers of polyethylene, copolymers of polypropylene, the copolymers of the monomers used to synthesize said polymers, or combinations thereof. The naturally occurring polymers may include chitin, algin, a starch, dextran, collagen, albumen, combinations thereof. The synthetic polymers may include polyethylene, polypropylene, a metallocene polymer, a polyurethane, a polyvinylchloride polymer, a polyester, a polyamide, or combinations thereof.

In one embodiment, the compressed composite sponge has a degree of adhesion to the wound site of about 40 kPa to about 500 kPa. In one embodiment, the compressed composite sponge has a degree of adhesion to the wound site of about 60 kPa to about 250 kPa. In one embodiment, the compressed composite sponge has a degree of adhesion to the wound site of about 100 kPa to about 200 kPa. The compressed composite sponge is capable of forming an adhesive material in combination with blood flowing from the wound at a wound dressing-blood interface. In one embodiment, the adhesive material is a chitosan adhesive material.

In one embodiment, the chitosan adhesive material has a pH of not more than about 6.3 when the wound is sealed. In one embodiment, the chitosan adhesive material has a pH of not more than about 4.5 when the wound is sealed. In one embodiment, the chitosan adhesive material has a pH of not more than about 4.0 when the wound is sealed.

The adhesive material may comprise an acid selected from the group consisting of acetic acid, formic acid, lactic acid, ascorbic acid, hydrochloric acid and citric acid. In one embodiment, the compressed composite sponge has a thickness that is not less than about 3.0 mm and not more than about 8 mm. In one embodiment, the compressed composite sponge has a thickness that is not less than about 3.5 mm and not more than about 7 mm. In one embodiment, the compressed composite sponge has a thickness that is not less than about 4.0 mm and not more than about 6 mm. In one embodiment, the compressed composite sponge has an ultimate tensile stress about 0.1 MPa to about 10 MPa. In one embodiment, the compressed composite sponge has an ultimate tensile stress of about 0.15 MPa to about 0.8 MPa. In one embodiment, the compressed composite sponge has an ultimate tensile stress of about 0.25 MPa to about 0.5 MPa. In one embodiment, the compressed composite sponge has an ultimate elongation of about 5%. In one embodiment, the compressed composite sponge has an ultimate elongation of about 10%. In one embodiment, the compressed composite sponge has an ultimate elongation of about 15% along with 2-octyl cyanoacrylate, which provides a skin adhesive as a sutureless surgery solution.

In one embodiment, a process for preparing a compressed sponge for hemorrhage control comprises: (a) freezing/freeze drying preparation of a low density sponge; and (b) compressing the low density sponge at a rate of about 10 mm per minute and at a controlled temperature of 80° C., thereby obtaining a compressed sponge with a density of about 0.1 to about 0.2 g/cm$^3$.

In one embodiment, a process for preparing a compressed sponge for hemorrhage control comprises: (a) preparing a low density sponge by methods other than freezing/freeze drying, and (b) compressing the subsequent low density sponge at a rate of about 10 mm per minute and at a controlled temperature of about 80° C., thereby obtaining a compressed sponge with a density of about 0.1 to about 0.2 g/cm$^3$. In one embodiment, the low density sponge has a density of about 0.01 g/cm$^3$ to about 0,035 g/cm$^3$. In one embodiment, the compressed sponge has a density of about 0.1 g/cm$^3$.

In one embodiment, a process for preparing a compressed composite sponge for hemorrhage control comprises: a) degassing chitosan/Poly L-Lysine biomaterial solution by heating the chitosan/Poly L-Lysine biomaterial solution and applying a vacuum thereto; b) freezing the chitosan/Poly L-Lysine biomaterial solution; c) removing water from within frozen chitosan biomaterial without damaging the structural integrity of the frozen chitosan/Poly L-Lysine biomaterial so that the water in the chitosan biomaterial passes from a solid phase into a gas phase; d) compressing the chitosan/Poly L-Lysine biomaterial at a rate of about 10 mm per minute thereby obtaining a compressed sponge with a density of about 0.1 to about 0.2 g/cm$^3$ and e) baking the compressed chitosan/Poly L-Lysine sponge at 80° C. for 30 minutes. In one embodiment, the temperature is gradually lowered over a predetermined period of time during the freezing of the chitosan/Poly L-Lysine biomaterial in step (b).

In one embodiment, the temperature of step (b) is a final freezing temperature of not more than about −25° C. In one embodiment, the process of step (b) involves final freezing temperature of not more than about −35° C. In one embodiment, the temperature of step (b) is a final freezing temperature of not more than about −45° C. The water removal may be performed by freeze-drying the frozen chitosan/Poly L-Lysine biomaterial. The process may further comprise a step of adding argon, nitrogen and helium hack into the degassed chitosan/Poly L-Lysine solution before the freezing.

The compressed sponge may be sterilized. In one embodiment, the compressed sponge is sterilized by gamma irradiation.

In one embodiment, a method of preventing severe bleeding in a subject comprising administering a compressed sponge or a compressed composite sponge is provided. In one embodiment, the subject is a mammal. In one embodiment, the mammal is human. In one embodiment, the subject is suffering from severe bleeding such that about 30-40% total blood volume loss would result within 20 to 30 minutes if the bleeding was left uncontrolled. In one embodiment, the compressed sponge or compressed composite sponge is applied with about 60 to 80 kPa pressure directly over the bleeding injury and held in place for 3 to 5 minutes before releasing, packing and wrapping.

In one embodiment, a bandage kit for treating severe bleeding comprising a compressed sponge or a composite compressed sponge, gauze rolls for packing and an Ace bandage for wrapping a wound is provided. In one embodiment, a process for mechanical mating and meshing of the compressed or composite compressed sponges comprises: pressing tissue contacting sides of the sponge against a macro-textured surface. The macro-textured surface may include surfaces prepared by chemical etching, surfaces prepared by ion beam surface ablation, surfaces prepared by mechanical cutting, and surfaces prepared by laser ablation.

In one embodiment, a process for improving the mechanical traction of the compressed or compressed composite sponges comprises: pressing tissue contacting sides of the sponge against a macro-textured surface. In one embodiment, the macrotextured surface is prepared by chemical etching or by particle blasting techniques.

In one embodiment, a process for limiting or stopping the formation of coarse crust on the surface of the composite or compressed composite sponges comprises: covering the surface of the sponge with a polymer film, a polymer plate, an elevated plastic plate or a moisture impermeable, breathable membrane film.

In one embodiment, a low density sponge is formed by compressing a sponge with an initial density of about less than 0.05 g/cm$^3$ until the sponge reaches a density of about less than 0.08 g/cm$^3$. The sponge can be formed by a process other than freezing or freeze drying. In one embodiment, the sponge is formed using a phase inversion process, covalent binding of active components to preformed matrices, or foaming techniques.

In one embodiment, a compressed sponge for hemorrhage control comprises a hydrophilic polymer, wherein the compressed sponge has a compressed sponge density of about 0.6 to 0.15 g/cm$^3$ and the hydrophobic polymer may be polyacrylic acid. It one embodiment, the compressed sponge may further comprise an active ingredient. The active ingredient may include, but is not limited to, calcium, thrombin, factor VIIa, factor XIIIa, Norepinephrine, epinephrine, growth factors, penicillin, ampicillin, methicillin, amoxicillin, clavamox, clavulanic acid, amoxicillin, aztreonam, imipenem, streptomycin, Kanamycin, Tobramycin, gentamicin, vancomycin, clindamycin, erythromycin, polymyxin, bacitracin, amphotericin, nystatin, rifampicin, tetracycline, doxycycline, chloramphenicol, or combinations thereof.

In one embodiment, a compressed composite sponge for hemorrhage control comprises a hydrophilic polymer sponge and a wettable polymer matrix or wettable polymer matrices inside the sponge and/or at the sponge surface, wherein the hydrophobic polymer is polyacrylic acid. The wettable polymer matrices may include non-woven mats, woven mats, molded polymer mesh and/or low density sponges. The wettable polymer matrix may include a chitin, an alginate, a neutralized chitosan, a re-acetylated chitosan, a poly(glycolic acid), a poly(lactic acid), a poly(e-caprolactone), a poly(β-hydroxybutyric acid), a poly(β-hydroxyvaleric acid), a polydioxanone, a poly(ethylene oxide), a poly(malic acid), a poly(tartronic acid), a polyphosphazene, a polyethylene, a polypropylene, a metallocene polymer, a polyurethane, a polyvinylchloride polymer, a polyester, a polyamide, or combinations thereof.

The sponge may comprise a textile thread impregnated with a hydrophilic polymer. In one embodiment, the textile thread is impregnated with a hydrophilic polymer, wherein the hydrophobic polymer is polyacrylic acid. In one embodiment, the wettable polymer matrices is a non-woven mesh. In one embodiment, the compressed composite sponge has a degree of adhesion to the wound site of at about 40 kPa to 500 kPa along with 2-octyl cyanoacrylate, which provides skin adhesive as a sutureless surgery solution.

The compressed composite sponge may be capable of forming an adhesive material in combination with blood flowing from the wound at a wound dressing-blood interface. In one embodiment, the compressed composite sponge has an ultimate elongation of about 10%. In one embodiment, the compressed composite has an ultimate elongation of about 15%.

In one embodiment, a process for preparing a compressed sponge for hemorrhage control comprises the steps of: (a) freezing/freeze drying preparation of a low density sponge; and (b) compressing the low density sponge at a rate of 10 mm per minute and at a controlled temperature of 80° C., thereby obtaining a compressed sponge with a density of about 0.1 to about 0.2 g/cm$^3$.

In one embodiment, a method of preventing severe bleeding in a subject comprises: administering a compressed sponge or a compressed composite sponge. In one embodiment, the subject is a mammal. In one embodiment, the mammal is human. In one embodiment, the subject is suffering from severe bleeding such that about 30-40% total blood volume loss would result within 20 to 30 minutes if the bleeding were left uncontrolled. In one embodiment, the compressed sponge or compressed composite sponge is applied with about 60 to 80 kPa pressure directly over the bleeding injury and held in place for 3 to 5 minutes before releasing, packing and wrapping the wound.

In one embodiment, a method for preventing severe bleeding in a subject comprises: administering a compressed sponge or a compressed composite sponge. In one embodiment, the subject is a mammal.

In one embodiment, a bandage kit for treating severe bleeding comprises: a compressed sponge or a composite compressed sponge, gauze rolls for packing and an Ace bandage for wrapping a wound.

The hydrogel micro-composite containing chitosan/Poly L-Lysine, hyaluronic/alginate (10/2/1) ratio resulted in significant acceleration of platelet/fibrin clot formation versus control (P<0.05). The addition of thrombin, tranexamic acid, and epinephrine to the micro-composite (Hemostat V) resulted in the fastest (shortest time to clotting, R), and strongest (MA) generation of platelet/fibrin clot even in the absence or the presence of high dose of the anticoagulant heparin (P<0.001). Further proof of the concept was confirmed using a hemorrhage simulation model system using the Hemostat V plus acrylate polymer derivative as a sealant (Hemostat V Seal). Data showed that deep injury into tissues resulted in blood loss at a rate of 100 ml/minute, which was stopped within 5-10 second upon the application of the Hemostat V Seal. Thus, the Hemostat V Seal formulated in gel, spray or bandage is useful in wide ranges of applications in stopping severe bleeding and saving lives.

Example 1: Hepatic Hemorrhage Control in Swine Liver Model

There is no universal animal model for testing efficacy of a topical hemostat available because trauma bleeding presents itself in different forms ranging from arterial injury with high pressure to massive oozing. Large animal models (e.g., pigs) are representative models for the human situation.

Liver injuries were induced. The method included the following. The liver was retracted by manually elevating the left and right medial lobes to allow adequate exposure. Next, a specially designed clamp with two 4.5 cm sharpened tines configured in the form of an 'X' was positioned with the center approximately 2-3 cm dorsal to the intersection of the left and right medial lobes, on the diaphragmatic surface of the liver. The base plate of the instrument was positioned beneath the quadrate lobe, on the visceral surface. The injury was induced by clamping the tines of the instrument through the parenchyma and underlying vessels of the two medial lobes so that the tines were seated in corresponding grooves in the base plate of the instrument. After the first penetration of the liver, the instrument was opened and the tines were withdrawn and repositioned to the animals left such that the second application would overlap the first by 50 percent. Following this repositioning, the liver was penetrated a second time. Documentation of the liver injury was achieved by excision and inspection of the liver at the conclusion of the experimental period. The injuries appeared as large stellate wounds with a small island of tissue in the center, and measured approximately 10×8×4 cm. The injuries were through and through, with one or more of the left medial lobar vein, right medial lobar vein, and portal hepatic vein lacerated.

Thirty seconds after injury, resuscitation was initiated with warm (38° C.) lactated Ringer's solution in all animals. The goal of resuscitation was return to baseline MAP. Fluid was administered at 260 mL/min. This resuscitation regimen was continued until the goal was reached and reinitiated if MAP decreased, throughout the 60 minute study period.

Simultaneously with initiation of resuscitation (30 seconds post-injury), treatments were applied as follows. One dressing was applied to the surface of the quadrate lobe to cover the penetrating injury and two other dressings were stuffed into the injury from the diaphragmatic aspect. Compression was applied for 60 seconds in the dorso-ventral direction. After 60 seconds, the injury was inspected to determine whether hemostasis was achieved. Next, the applicator's hands were repositioned and pressure was applied for 60 seconds in the latero-medial direction, and the observation for hemostasis was performed. This sequence was repeated for a total of four 60 second compressions. If hemostasis was complete after any compression, no further compressions were performed. Hemostasis was defined as the absence of visually detectable bleeding from the injury site.

Example 2

Thrombelastography (Clot Kinetics)

Thrombelastography techniques, which are commonly used in the clinical laboratory for monitoring coagulation functions, were utilized. Siliconized Vacutainer tubes (Becton Dickinson, Rutherford, N.J.) were used to collect whole blood. To maintain a ratio of citrate to whole blood of 1:9 (v/v), the tubes contained 3.2% trisodium citrate. Blood samples were placed on a slow speed rocker until TEG analysis.

Thrombelastography (TEG)

Whole Blood Coagulation Analyzer, Model 5000 Thrombelastograph, Hemoscope Corporation, Skokie, Ill., was used. TEG is based on the measurement of the physical viscoelastic characteristics of blood clots. An oscillating plastic cylindrical cuvette ("cup") and a coaxially suspended stationary piston ("pin") with a n clearance between the surfaces are used to monitor clot formation at 37° C. Every 4.5 seconds, with a 1-second mid cycle stationary period, the cup oscillates in either direction, resulting in a frequency of 0.1 Hz. A torsion wire that acts as a torque transducer suspends the pin. Fibrin fibrils link the cup t the pin during clot formation, and the rotation of the cup is transmitted to the pin via the viscoelasticity of the clot (Ghavidel A A, Toutounchi Z, Shahandashti F J, Mirmesdagh Y. (2015), Rotational thromboelastometry in prediction of bleeding after cardiac surgery, Asian Cardiovascular Thoracic Ann pii: 0218492314566330). Customized software (Hemoscope Corporation, Skokie, Ill.) and an IBM-compatible personal computer display the rotation. The pin's torque is plotted as a function of time, as shown by the different TEG clot parameters.

Different hydrogel polycatioinic matrix micro-composites were evaluated. The hydrogel polycatioinic matrix micro-composites contained intrinsic, extrinsic coagulation pathways, and platelet activators in accelerating blood platelet-fibrin clotting.

Table 1 depicts a composition of various matrix composites along with coagulation pathway and platelet activators.

TALBE 1

| Composition | Chitosan | Hyaluronic Acid | Alginic Acid | TXA | Thrombin | $CaCl_2$/ Kaolin | Epi-nephrine |
|---|---|---|---|---|---|---|---|
| Matrix (M) | 100 mg | 20 mg | 10 mg | | | | |
| M + Kaolin | 100 mg | 20 mg | 10 mg | | | 5 mg | |
| M + TXA + K | 100 mg | 20 mg | 10 mg | 20 mg | | 5 mg | |
| M + T + K | 100 mg | 20 mg | 10 mg | | 10 units | 5 mg | |
| M + TXA + T + K | 100 mg | 20 mg | 10 mg | 20 mg | 10 units | 5 mg | |
| M + K + EP | 100 mg | 20 mg | 10 mg | | | 5 mg | 10 mg |
| M + TXA + K + EP | 100 mg | 20 mg | 10 ma | 20 mg | | 5 mg | 10 mg |
| M + TXA + T + K (Hemostat) | 100 mg | 20 mg | 10 mg | 20 mg | 10 units | 5 mg | |
| M + TXA + T + K + EP(Hemostat V) | 100 mg | 20 mg | 10 mg | 20 mg | 10 units | 5 mg | 10 mg |
| M + TXA + K + EP | 100 mg | 20 mg | 10 mg | 20 mg | | 5 mg | 10 mg |

In Table 1, TXA=tranexamic acid, final volume for all composites=1.5 ml+1.5 ml, and Matrigel® (Fibrin/Laminin/Collagen/Growth Factors)=3 ml. In Table 1, cross-bridging between the polycation chitosan/Poly L-Lysine and the polyanionic hyaluronic and alginic acids forms an amide bond and thus provide a hydrogel matrix for the inclusion of the various coagulation and platelet activators, vasoconstrictors, and wound sealants.

Example 3: Synthesis of Nano-Composites

The synthesized nano-composites have a size in a range of 100 nm to 1000 nm.

Cross linkage of chitosan/Poly L-Lysine to hyaluronic-alginic acid polymer was carried out where the nanoparticles encapsulating active compounds listed in Table 1 along with antimicrobial, pro-angiogenesis, and/or local anesthetic was synthesized by ionic gelatin method. To 15 ml solution of hybrid chitosan/Poly L-Lysine-hyaluronic-alginic acid polymer (5 mg/ml in DI water), 2 ml of active pro-coagulant compounds listed in Table 1, with or without (antibiotic, Lidocaine, pro-angiogenesis agent; 5 mg/ml in DI water), was added and stirred for half an hour. To this entire solution, 3 ml TPP (1 mg/ml in DI water) was added drop by drop and the entire solution was stirred for about 4 hours. This solution containing the nanoparticles was dialyzed using 20 KDa membrane to remove the un-reacted and non-encapsulated (active compounds). The dialyzed solution containing the nanoparticles was freeze dried to get the nano-composites in powdered form and can be used for further study. The nano-composites were dispensed in Matrigel® (liquid at 4 degree Centigrade) or phosphate buffered saline for testing.

FIG. 1 depicts nano- or micro-composites encapsulating active pro-coagulants listed in Table 1 with or without local anesthetic (e.g., Lidocaine), antibiotics and/or angiogenesis stimulating agent (e.g., growth factors plus sulfated oligosaccharide), for topical or implant applications, in accordance with embodiments of the present invention.

FIG. 1A depicts synthesis of a hydrogel matrix, said hydrogel matrix comprising naturally driven mushroom chitosan ionically bonded to both hyaluronic acid and alginic acid, said hydrogel matrix encapsulating various compounds, in accordance with embodiments of the present invention. The synthesis is performed in a presence of Sodium tripolyphosphate.

FIG. 1B depicts synthesis of a hydrogel matrix, said hydrogel matrix comprising naturally driven mushroom chitosan covalently bonded to both hyaluronic acid and alginic acid, said hydrogel matrix encapsulating various compounds, in accordance with embodiments of the present invention. The synthesis is performed in a presence of 1-Ethyl-3-(3-dimethylaminopropyl) carbodiimide (EDC).

FIG. 2A depicts synthesis of a hydrogel matrix, said hydrogel matrix comprising poly L-Lysine ionically bonded to both hyaluronic acid and alginic acid, said hydrogel matrix encapsulating various compounds, in accordance with embodiments of the present invention. The synthesis is performed in a presence of Sodium tripolyphosphate (TPP).

FIG. 2B depicts synthesis of a hydrogel matrix, said hydrogel matrix comprising poly L-Lysine covalently bonded to both hyaluronic acid and alginic acid, said hydrogel matrix encapsulating various compounds, in accordance with embodiments of the present invention. The synthesis is performed in a presence of 1-Ethyl-3-(3-dimethylaminopropyl) carbodiimide (EDC).

FIG. 3A depicts synthesis of a hydrogel matrix, said hydrogel matrix comprising naturally driven mushroom chitosan and poly L-Lysine ionically bonded to both hyaluronic acid and alginic acid, said hydrogel matrix encapsulating various compounds, in accordance with embodiments of the present invention. The synthesis is performed in a presence of Sodium tripolyphosphate (TPP).

FIG. 3B depicts synthesis of a hydrogel matrix, said hydrogel matrix comprising naturally driven mushroom chitosan and poly L-Lysine covalently bonded to both hyaluronic acid and alginic acid, said hydrogel matrix encapsulating various compounds, in accordance with embodiments of the present invention. The synthesis is performed in a presence of 1-Ethyl-3-(3-dimethylaminopropyl) carbodiimide (EDC).

A hydrogel matrix of the present invention comprises chitosan and/or poly L-Lysine ionically or covalently bonded to both hyaluronic acid and/or alginic acid, wherein the hydrogel matrix encapsulates various compounds. The ionic bond is formed using TPP (see FIGS. 1A, 2A, 3A). The covalent amide bond (CO—NH) is formed using EDC via dehydration or condensation synthesis covalently linking chitosan (CH) and/or Poly L-Lysine (PL) with hyaluronic (HA) and/or alginic (AL) acids resulting in CH/PL-acid cross linked polymer for nano or micro composite scaffold depending on the molecular weight of CH and PL.

In FIGS. 1A, 1B, 2A, 2B, 3A, and 3B, the compounds being encapsulated by the hydrogel matrix may include, inter cilia, activators of coagulation (e.g., thrombin, tranexamic acid), a calcium salt (such as calcium chloride) with or without Kaolin, a platelet activator, a vasoconstrictor/e.g., epinephrine, norepinephrine), a sealant (e.g., a cyanoacrylate such as 2-octyl cyanoacrylate), wound healing accelerators (e.g., angiogenesis stimulators), a local anesthetic (e.g., Lidocaine), a broad spectrum antibiotic, an anti-fibrinolysis compound (e.g., tranexamic acid).

Table 2 depicts molecular weight ranges of mushroom chitosan, and Table 3 depicts molecular weight ranges of poly L-Lysine.

TABLE 2

Chitosan Molecular Weight Ranges

| Chitosan (Mushroom) | Molecular Weight (Dalton) |
| --- | --- |
| Ultra-Low Molecular Weight Chitosan | 20,000-30,000 |
| Low Molecular Weight Chitosan | 40,000-60,000 |
| Medium Molecular Weight Chitosan | 60,000-120,000 |
| Medium to High Molecular Weight Chitosan | 110,000-150,000 |
| High Molecular Weight Chitosan | 140,000-220,000 |

For Nano-Composite (100 to less than 1000 nm), Ultra-Low, Low and Medium Molecular Weight Chitosan are used. For Micro-Composite (1-10 μm), Medium to High and High Molecular Weight Chitosan are used.

TABLE 3

Poly L-Lysine (PL) Molecular Weight Ranges

| Poly L-Lysine | Molecular Weight (Dalton) |
| --- | --- |
| Low Molecular Weight PL | 30,000-70,000 |
| Medium Molecular Weight PL | 70,000-150,000 |
| Medium to High Molecular Weight PL | 150,000-300,000 |
| High Molecular Weight PL | >300,000 |

For Nano-Composite (100 to less than 1000 nm), Low and Medium Molecular Weight PL are used. For Micro-Composite (1-10 μm), Medium to High and High Molecular Weight Chitosan are used.

Example 4: Encapsulation of Active Agents

An example is Local anesthetic=(Lidocaine, L), and/or pro-angiogenesis agent=(growth factors).

Example 5: Characterization of Nanoparticles

The size and size distribution of CHI-HA-NPs was determined using a Malvern zeta sizer (Malvern Instrumentation Co., Westborough, Mass., USA). 2 ml of the nanoparticle solution was placed in a 4-sided, clear plastic cuvette and was directly analyzed at 25° C. Similarly, size and morphology of this nanoformulation was measured by TEM.

Example 6: Analysis of the Amount of Active Drug in Nanoformulations

The amount of active drug was determined by disintegrating the nanoparticles and measuring the active drug by established LC/MS/MS methods.

At present, lidocaine and other Caine drugs are used for anesthesia and analgesia. These drugs target nerve endings responsible for pain generation. The use of the lidocaine and other Caine drugs has become ubiquitous for helping to control such pains. In many cases, a prolonged pain relief drug effect would be preferred. Injection of longer lasting lidocaine into the epidural space, spinal and musculoskeletal joints and even acute fractures would enhance pain control and diminish the need for more systemic methods. As more experience is gathered, when pain is blocked, a more successful attempt can be made to allow for conditioning and strengthening efforts. The potential of lidocaine lasting much longer than is presently possible would be appealing. In the spine disease arena, the placement of medicine into the affected area is most important but the amount of time the medicine is able to act has not before been easily manipulated. The use of epidural injection and spinal injections such as medial branch block, trigger point injection, disc injections as well as facet blocks are used to pinpoint, target and treat a suspected pain generating area. This can also be done for musculoskeletal joints such as knee, shoulder, hip, sacroiliac, elbow, wrist, ankle, hand and foot. This family of medicine temporarily maps and extinguishes the site from which pain may be emanating. The ability to attain long term pain relief might allow for the pain generator to be masked and have a chance for improvement. Today, musculoskeletal and spinal pain may be paroxysmal and often seen as to come and go. This potential pain relieving period allows for neighboring muscle, ligament and tendon to undergo painless time for conditioning. This would also allow the biochemical and biomechanical environment of the affected pain generating area to have a chance to evolve and change and possibly to see some improvement, albeit paroxysmal.

The ability to have longer lasting pain relief over a prolonged period of time without having to re-administer dosing is appealing.

In cases of acute injury or painful degeneration and inflammation, such a treatment as slow long term release of medicine would allow for repair, regeneration or reestablishment of involved structures to a more functional existence.

Example 7: Testing Effects of Nano- or Micro-Composites on Clot Kinetics Using Thrombelastography FIG. 4 depicts a representative tracing by a Thrombelastography (TEG) system used in the current study (total of 4 TEGs with 2 channels each), in accordance with embodiments of the present invention.

Key kinetic parameters in the representative tracing in FIG. 4 include R (lag time to clot initiation in minutes) and MA (clot strength in mm) as shown.

FIG. 4 also depicts characteristic thrombelastograph tracings (normal, thrombocytopenia, severe platelet dysfunction, coagulation factor, deficiency, fibrinolysis, hypercoagulable state) showing the platelet/fibrin clot kinetic under various clinical disorders.

A standard global coagulation assay, namely Thrombelastography, uses a total of 5 ml blood from human volunteers. Additionally, the efficiency of the optimal hydrogel compositions that have the shortest Time to Clotting (R) and the strongest clot strength (MA) were evaluated in stopping severe bleeding in a hemorrhage simulation model system.

Example 8: Reproducibility of TEG Tracings

FIG. 5 depicts representative clot kinetic parameters (R, K, Angle, MA, CI) and tracings for blood obtained from the same subject, and read in the 4 TEGS (2 channels each), in accordance with embodiments of the present invention. Representative tracings for the platelet fibrin clot kinetic for multiple channels read out for blood sample obtained from the same subject is shown in FIG. 5.

Example 9: Hemorrhagic Bleeding Simulation Model—Wound Synthoclot Test

FIG. 6 depicts use of a simulation model system, in accordance with embodiments of the present invention. The simulation model system is used to test the Hemostat V Seal (micro-composite containing kaolin, tranexamic acid, thrombin, calcium, epinephrine and cyanoacrylate).

Fresh meat is placed in a tray. An outflow tubing is placed and threaded through the meat, ensuring that a sinusoid is centrally placed in the meat. Heparinized blood is run for 3-5 minutes for blood perfusion through the simulation model. The flow is made continuous and with no air bubbles to avoid occluding the line. When incisions are made in the meat, the peristaltic perfusion pump kept running to simulate in situ conditions.

Example 10: Thrombelastography and Clot Kinetics

The hydrogel micro-composite containing chitosan/Poly L-Lysine/hyaluronic/alginate (10/2/1) resulted in significant acceleration of platelet/fibrin clot formation versus control ($P<0.05$). The addition of thrombin, anexamic acid, and epinephrine to the micro-composite (Hemostat V) resulted in the fastest (shortest time to clotting, R), and strongest (MA) generation of platelet/fibrin clot even in the absence of high dose of the anticoagulant heparin ($P<0.001$).

Data showed that the presence of chitosan/Poly L-Lysine in the micro composite was effective in accelerating clot initiation (i.e., shortening time to clotting, R). Chitosan/Poly L-Lysine is known to have a both platelet promoting activity and antimicrobial effects, which might explain the impact of chitosan Poly L-Lysine on acceleration of clotting (see FIG. 7).

Example 11: Statistical Analysis

Data represent mean±standard deviation, n=4 per group, and statistical analysis was carried out using Student t-test (Stat View) for paired comparison between the control and the different treatment groups and the differences among the different treatment groups were further compared to each other using one way analysis of variance (ANOVA); $P<0.05$ is the cut off for statistical significance.

Table 4 depicts the effect of the different Hemostat V compositions on clot kinetic. Table 4 shows the platelet/ fibrin clot promoting activity for the various components within the Hemostat V formulation.

TABLE 4

| Hemostatic V Composition | R - Time to Clot initiation (Minutes) | MA-Clot Strength (mm) |
|---|---|---|
| Control | 12.5 ± 3 | 57 ± 5 |
| Alginic Acid (AA) | 12.0 ± 4 | 58 ± 4 |
| Chitosan (CH) | 7.2 ± 2* | 56 ± 5 |
| Poly L-Lysine (PL) | 6.4 ± 1* | 61 ± 4 |
| Hyaluronic Acid (HA) | 10.0 ± 3 | 62 ± 6 |
| Kaolin (K) | 7.5 ± 2 | 55 ± 5 |
| tranexamic acid (TXA) | 9.0 ± 4 | 57 ± 4 |
| M (CH/HA/AA) | 4.2 ± 0.8** | 59 ± 4 |
| M (PL/HA/AA) | 2.8 ± 0.8** | 65 ± 4 |
| Thrombin (T) (10 units) | 1.9 ± 0.3** | 61 ± 4 |
| Heparin (10 µg) | >60.00 | 0.00 |
| Heparin + (M)/K/TXA/T | 0.9 ± 0.2** | 58 ± 5** |
| Heparin + (M) | | |
| Heparin + (M)/Epinephrine (EP) | 2.5 ± 0.8** | 65 ± 3 |
| Heparin + (M) + Ep/K/TXA/T | 0.1 ± 0.0** | 72 ± 4** |

*P < 0.05 Chitosan versus control,
**P < 0.001 thrombin versus control,
**P < 0.001 Matrix polymer composite containing tranexamic acid and thrombin + Heparin versus Heparin,
**P < 0.001 Matrix polymer composite versus control.

The control (1) in Table 4 is use of normal blood (i.e., nothing added to the blood).

FIG. 7 depicts the effect of matrix composites on human blood coagulation kinetics, in accordance with embodiments of the present invention. The control in FIG. 7 is use of normal blood (i.e., nothing added to the blood).

The data in FIG. 7 shows significant acceleration of clot generation with the four different matrix composites (R=7.8, 5.9, 6.8, 10 min) versus the control (R=12.8 min). The three different matrix composites within the Hemostat V product also have higher clot strength (MA=63.5, 64.0, 62.5, 59.3 min) versus the control (MA=58.6).

FIG. 8 depicts the effect of Hemostat and Hemostat V composition on clot initiation kinetic (R) and clot strength (MA), in accordance with embodiments of the present invention. Hepatin 4 µg is the control used if the Hemostat and Hemostat V compositions. The Hemostat and Hemostat V compositions reduced R to 7.8 and 10.8 min, respectively, from R=60.7 min for the Heparin 4 µg control. The Hemostat and Hemostat V compositions increased MA to 61.0 and 63.3 mm, respectively, from MA=27.8 mm for the Heparin 4 µg control.

FIG. 9 depicts the effect of Hemostat V on reversing time to clot initiation (R), in accordance with embodiments of the present invention. The control in FIG. 9 is use of normal blood (i.e., nothing added to the blood). FIG. 9 shows R reduced from about 12 minutes (control) to about 4 minutes (M+E) and about 2 minutes (M+E+T), respectively.

FIG. 10 depicts the effect of Hemostat V composition on time to clot for blood loss in severe hemorrhage simulation model with heparin (10 µg) as a control, in accordance with embodiments of the present invention. The Hemostat V composition reduces R from about 60 minutes (control) to a negligible value (of the order of seconds) with use of Hemostat V.

FIG. 11 depicts the effect of Hemostat V composition on clot strength with heparin (10 µg) as a control, in accordance with embodiments of the present invention. The Hemostat V composition increases MA from about 52 in (control) to about 70 mm with use of Hemostat V.

Further proof of the concept for the efficiency of the optimal formulation was confirmed using a hemorrhage simulation model system using the Hemostat V plus acrylate polymer derivative as a sealant (Hemostat V Seal). Data showed that deep injury into tissues resulted in blood loss at a rate of 100 ml/minute, which was stopped within 5-10 second upon the application of the Hemostat V Seal (FIG. 12).

FIG. 12 depicts the effect of Hemostat V Seal on blood loss in simulation model, in accordance with embodiments of the present invention.

As to formulations of Hemostat V-Seal (HVS), hemostatic agents in HVS could be prepared in hydrogel matrix that is liquid at when kept cool and forms a film at room temperature to seal the wound. Furthermore, hemostatic agents in HVS could be applied in dressings to stimulate clotting when placed on the wound.

Hemostat V-Seal stops blood loss secondary to severe hemorrhages, stops excessive bleeding pre, intra, or post various surgical procedures, stops excessive blood loss in patients taking anticoagulants or with blood deficiencies, accelerates wound healing, and prevents infection when adding antimicrobial agents.

Hemostat V-Seal devices are easy to use and stop bleeding with or without pressure bandages, providing stability in order to get patients to the next level of care.

Utility of Hemostat V-Seal Products include: (a) Trauma and Emergency Room, (b) Critical Care and Intensive Care, (c) Surgical Units, (d) Dental Clinics, (e) Wound Clinics (Cuts, Lacerations, and Abrasions), and (f) Burn Clinics.

The hydrogel micro-composite containing chitosan/Poly L-Lysine, hyaluronic acid, and alginate resulted in the significant acceleration of platelet/fibrin clot formation versus a control of normal human blood as well as a control of blood containing excess anti-coagulants. The addition of thrombin, kaolin, tranexamic acid, and epinephrine to the micro-composite (Hemostat V-Seal) resulted in the fastest (shortest time to clotting, R) and strongest (MA) generation of platelet/fibrin clots, even in the presence of high amounts of the anticoagulant heparin. In the hemorrhage simulation model system, severe injuries resulted in blood loss at a rate of 100 ml/minute, which was stopped within 5-10 seconds upon the application of the Hemostat V-Seal. Furthermore, a multifunctional hydrogel was prepared as a wound dressing designed to stop bleeding and improve healing (Hemostat V-Seal), inhibit infection (silver nanoparticles containing povidone iodine), and relieve pain (Lidocaine). Hemostat V-Seal is a multifunctional platform that exceeds many of the existing products that provide small improvements in the wound that is infected by various insults. For example, adding alginate to existing zeolite hemostat was shown to have improvement over Zeolite in swine model of battlefield injury. See Ghavidel A A, Toutounchi Z. Shahandashti Mirmesdagh Y. (2015), Rotational thromboelastometry in prediction of bleeding after cardiac surgery, Asian Cardiovascular Thoracic Ann pii: 0218492314566330. These and several other small improvements indeed provided incremental improvement but not as effective as the Hemostat V-Seal compositions of the present invention.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
   a hydrogel matrix comprising at least one polymer cross linked, via ionic or covalent bonding, with both hyaluronic acid and alginic acid,
   wherein the at least one polymer is selected from the group consisting of chitosan, poly L-Lysine, and a combination thereof,
   wherein a plurality of substances encapsulated within the matrix comprises thrombin functioning as an activator of coagulation and epinephrine functioning as a vasoconstrictor, and
   wherein the composition is characterized by a time to initiate clot formation with the composition added to blood being less by a factor of at least 6 than the time to initiate clot formation with a control of nothing added to blood to impact clot formation.

2. The composition of claim 1, wherein each polymer of the at least one polymer is ionically bonded to both the hyaluronic acid and the alginic acid.

3. The composition of claim 1, wherein each polymer of the at least one polymer is covalently bonded to both the hyaluronic acid and the alginic acid.

4. The composition of claim 1, wherein a linear size of the matrix is in a range of 100 nm to less than 1000 nm.

5. The composition of claim 1, wherein a linear size of the matrix is in a range of 1 μm to 10 μm.

6. The composition of claim 1, wherein the plurality of substances encapsulated within the matrix further comprises another activator of coagulation including tranexamic acid, a calcium salt, or a combination thereof.

7. The composition of claim 1, wherein the plurality of substances encapsulated within the matrix further comprises another vasoconstrictor including norepinephrine.

8. The composition of claim 1, wherein the plurality of substances encapsulated within the matrix further comprises a sealant.

9. The composition of claim 8, wherein the sealant comprises a cyanoacrylate.

10. The composition of claim 8, wherein the sealant is in a form of a dry powder, a spray, a gel, a sponge, a bandage, gauze, or combinations thereof.

11. The composition of claim 1, wherein the plurality of substances encapsulated within the matrix further comprise an angiogenesis stimulator, an anesthetic, an antibiotic, or combinations thereof.

12. A method, comprising:
    applying the composition of claim 1 to a site on or within a body of a mammal.

13. The method of claim 12, wherein the mammal is a human being.

14. The method of claim 12, wherein said applying the composition is implemented when the mammal is bleeding at the site, and wherein the composition is configured to reduce a time to initiate formation of a clot formed at the site relative to a control of nothing being administered at the site to stop the bleeding.

15. The method of claim 14, wherein the composition is further configured to increase a clot strength of the clot relative to the control.

16. The method of claim 14, wherein the site comprises a wound, and wherein said applying the composition comprises applying the composition to the wound.

17. The method of claim 16, wherein the composition is further configured to treat infection of the wound.

18. The method of claim 16, wherein the composition is further configured to accelerate healing of the wound.

19. The composition of claim 1, wherein the at least one polymer consists of chitosan and poly L-Lysine.

20. The composition of claim 1, wherein the plurality of substances encapsulated within the matrix further comprises tranexamic acid functioning as an anti-fibrinolysis compound and kaolin functioning as platelet activator, wherein the composition is characterized by the time to initiate clot formation with the composition added to the blood being less by a factor of at least 500 than the time to initiate clot formation with a control of heparin added to the blood.

21. The composition of claim 1, wherein the plurality of substances encapsulated within the matrix further comprises 2-octyl cyanoacrylate functioning as a sealant, wherein the composition is characterized by a volume of blood loss with the composition added to the blood being less by a factor of at least 80 than the volume of blood loss with a control of no sealant added to the blood.

* * * * *